(12) United States Patent
Dobashi et al.

(10) Patent No.: US 9,125,597 B2
(45) Date of Patent: Sep. 8, 2015

(54) OPHTHALMOLOGIC APPARATUS, AND OPHTHALMOLOGIC METHOD AND PROGRAM

(71) Applicant: CANON KABUSHIKI KAISHA, Tokyo (JP)

(72) Inventors: Yasuhiro Dobashi, Matsudo (JP); Toshiaki Okumura, Tokyo (JP); Koichi Ohta, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 294 days.

(21) Appl. No.: 13/711,935

(22) Filed: Dec. 12, 2012

(65) Prior Publication Data

US 2013/0162946 A1   Jun. 27, 2013

(30) Foreign Application Priority Data

Dec. 21, 2011 (JP) ................. 2011-279582
Dec. 21, 2011 (JP) ................. 2011-279586
Dec. 21, 2011 (JP) ................. 2011-279990
Dec. 6, 2012  (JP) ................. 2012-267288

(51) Int. Cl.
*A61B 3/14* (2006.01)
*A61B 3/00* (2006.01)
*A61B 3/15* (2006.01)

(52) U.S. Cl.
CPC ... *A61B 3/14* (2013.01); *A61B 3/00* (2013.01); *A61B 3/152* (2013.01)

(58) Field of Classification Search
CPC .. A61B 3/0025; A61B 3/0058; A61B 3/0033; A61B 3/10; A61B 3/1025; A61B 3/117; A61B 3/1241; A61B 3/1015; A61B 3/1233; A61B 3/14; A61B 5/02416; A61B 3/00; A61B 5/0261; A61B 3/145; A61B 3/152
USPC ......... 351/200, 205, 206, 209, 211, 221, 222, 351/243, 245, 246

See application file for complete search history.

(56) References Cited

U.S. PATENT DOCUMENTS 5,270,749 A   12/1993  Okumura
5,500,696 A *  3/1996  Masuda et al. ............... 351/205

(Continued)

FOREIGN PATENT DOCUMENTS

JP    7-016204 A   1/1995
JP   10-192334 A   7/1998

(Continued)

*Primary Examiner* — Joseph P Martinez
*Assistant Examiner* — Brandi Thomas
(74) *Attorney, Agent, or Firm* — Fitzpatrick, Cella, Harper & Scinto

(57) ABSTRACT

Provided is an ophthalmologic apparatus which is capable of performing offset adjustment of an alignment position while performing transillumination observation by automatic alignment. The ophthalmologic apparatus includes an automatic alignment unit for automatically performing alignment between a measuring portion and an eye to be inspected, and an alignment position changing unit capable of moving an optical axis center position of the measuring portion to an arbitrary position in the transillumination observation.

18 Claims, 16 Drawing Sheets

(56) References Cited

U.S. PATENT DOCUMENTS

| | | |
|---|---|---|
| 5,751,396 A | 5/1998 | Masuda et al. |
| 5,894,337 A | 4/1999 | Okinishi et al. |
| 6,030,376 A | 2/2000 | Arashima et al. |
| 6,192,269 B1 | 2/2001 | Okumura et al. |
| 6,193,372 B1 | 2/2001 | Okumura et al. |
| 6,324,420 B1 | 11/2001 | Kishida et al. |
| 6,332,683 B1 | 12/2001 | Ono et al. |
| 7,506,980 B2 | 3/2009 | Fujieda |
| 2008/0079899 A1 | 4/2008 | Fujieda |
| 2012/0218521 A1* | 8/2012 | Dobashi .................. 351/245 |

FOREIGN PATENT DOCUMENTS

| | | |
|---|---|---|
| JP | 2001-269316 A | 10/2001 |
| JP | 3244873 B2 | 1/2002 |
| JP | 2005-287752 A | 10/2005 |
| JP | 2005-312501 A | 11/2005 |
| JP | 2006-122411 A | 5/2006 |
| JP | 2008-080065 A | 4/2008 |
| JP | 4469205 B2 | 5/2010 |
| JP | 4481420 B2 | 6/2010 |

* cited by examiner

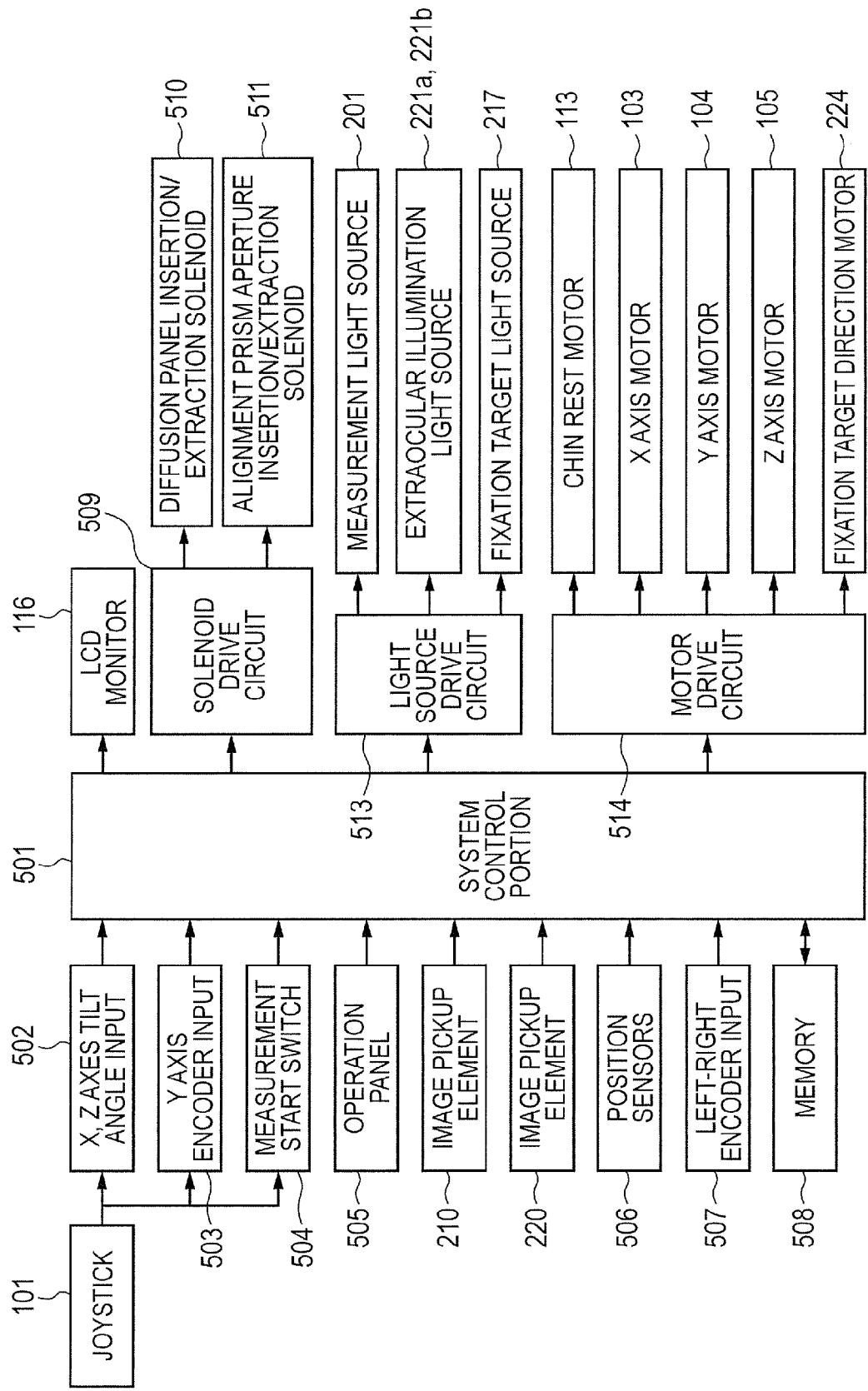

OPHTHALMOLOGIC APPARATUS, AND OPHTHALMOLOGIC METHOD AND PROGRAM

BACKGROUND OF THE INVENTION

1. Field of the Invention

The present invention relates to an ophthalmologic apparatus and an ophthalmologic method for measuring information on an eye to be inspected, such as eye refractive power of the eye to be inspected.

2. Description of the Related Art

Conventionally, in an ophthalmologic apparatus for measuring eye refractive power or the like of an eye to be inspected, there is known a method of observing a transillumination image as a measure against occurrence of a measurement error. Here, the transillumination image is an image obtained by observing a pupil area illuminated from inside of the eye to be inspected by reflection light of transillumination observation light projected to a fundus of the eye to be inspected. When a crystalline lens as a transparent body has opacity due to cataract or the like, the opacified portion is observed as a dark shadow. Therefore, observation of the transillumination image is used for investigating the cause of the measurement error or the like.

Japanese Patent No. 3,244,873 discloses an ophthalmologic apparatus that can perform the transillumination observation using a measurement light source without an additional light source for the transillumination observation. When a measurement error occurs, the mode is changed to a transillumination observation mode, in which alignment is manually performed so as to avoid the opacity in the crystalline lens. Then, the eye refractive power is measured again while performing the transillumination observation.

Japanese Patent No. 4,469,205 discloses an ophthalmologic apparatus in which an automatic alignment reference position is changed based on a transillumination still image picked up in advance, and the alignment is performed while avoiding the opacified portion in the crystalline lens due to cataract or the like. Usually, an alignment target position of a measuring portion with respect to the eye to be inspected is set to be matched with the pupil center. However, when the crystalline lens has opacity so that a ring image necessary for measuring ocular refraction is partially lost, the measurement cannot be performed in a normal alignment position. Therefore, in the invention disclosed in Japanese Patent No. 4,469,205, when a measurement error occurs, the measurement error is to be reduced by moving the alignment target position so that the ring image for measurement avoids the opacified portion while viewing the transillumination still image picked up in advance. After a new alignment position is determined, a measurement screen is displayed again so that the measurement is restarted.

In addition, in a conventional ophthalmologic apparatus for measuring the eye refractive power of the eye to be inspected, it is known to display a transillumination image after measuring the eye refractive power value as a countermeasure when the eye refractive power measurement is not correctly performed due to a disease such as cataract. In the invention disclosed in Japanese Patent No. 4,469,205, alignment is first performed based on a corneal reflex image, and light from a light source for transillumination observation is projected to the fundus so that an image is picked up and stored as a still image during preliminary measurement or fogging operation. Then, when a refractive power measurement error occurs, the transillumination image as a stored still image is displayed in an enlarged manner.

In addition, in the conventional ophthalmologic apparatus, before an acquiring portion acquires specific information of the eye to be inspected, such as eye refractive power, a fundus image, or fundus blood flow, alignment (positional adjustment) of the acquiring portion with respect to the eye to be inspected is performed. As to the alignment, there is known an apparatus which automatically performs the alignment of the acquiring portion with respect to the eye to be inspected, by projecting an alignment index light beam to the cornea of the eye to be inspected, detecting a reflection image of the cornea of the eye to be inspected in a photoelectric manner, and driving the acquiring portion in three axis directions based on the detected information.

Further, there is known an apparatus which performs alignment (positional adjustment) involving the pupil of the eye to be inspected in consideration of the fact that most human eyes to be inspected have the corneal apex decentered from the pupil center, although depending on individual differences or pathologic factors. Japanese Patent No. 4,481,420 proposes an apparatus which detects a pupil position by utilizing the fact that the pupil portion is darker than other portions, and performs the alignment with the pupil center position when there is a difference between the alignment position based on an index image by cornea reflection and the pupil center position.

However, as to the ophthalmologic apparatus as described in Japanese Patent No. 3,244,873, it is necessary to manually perform the alignment during observation of the transillumination image. Therefore, it is difficult to maintain a positional relationship with the eye to be inspected while performing the measurement, and the operation becomes difficult. The ophthalmologic apparatus described in Japanese Patent No. 4,469,205 performs the change of the alignment position when measuring an ocular refractive index based on information of the transillumination still image. Therefore, there is a problem that desired alignment accuracy cannot be obtained when a fixation position of the eye to be inspected is different between when the ocular refractive index is measured and when the transillumination image is acquired. In addition, there is a problem that the measurement time is increased because the transillumination image is retrieved for correcting the alignment position every time a measurement error occurs. Further, there is a problem that the transillumination observation at a time point when the refractive power measurement error occurs cannot be performed, because the transillumination image is displayed as a still image without synchronization with occurrence of the refractive power measurement error.

In addition, the ophthalmologic apparatus as described in Japanese Patent No. 4,481,420, in which a dark portion is recognized as a pupil, has a problem that the pupil area is erroneously determined when lashes or the like overlap the pupil as a dark portion, and hence desired alignment accuracy cannot be obtained.

SUMMARY OF THE INVENTION

It is an object of the present invention to provide an ophthalmologic apparatus and an ophthalmologic method which enable improvement of operability in the transillumination observation and reduction of measurement time.

According to an exemplary embodiment of the present invention, there is provided an ophthalmologic apparatus including; a measuring unit which measures information on an eye to be inspected by illuminating the eye to be inspected, a driving unit which drives the measuring unit, a transillumination moving image acquiring unit which acquires a transillumination moving image of the eye to be inspected, a display control unit which controls a display unit to display the transillumination moving image, a changing unit which changes a reference position for performing alignment between the eye to be inspected and the measuring unit in the transillumination moving image displayed on the display unit; and a control unit which controls the driving unit so as to perform the alignment by using the changed reference position.

Further, according to another exemplary embodiment of the present invention, there is provided an ophthalmologic apparatus including; an acquiring unit which acquires an image on a fundus of an eye to be inspected, an acquiring unit which acquires an image on an anterior ocular segment of an eye to be inspected, a transillumination moving image acquiring unit which acquires a transillumination moving image of the eye to be inspected; and a control unit which controls the transillumination moving image acquiring unit to acquire the transillumination moving image in a case where information of the fundus in the acquired image on the fundus is partially lost.

According to the present invention, it is possible to perform offset adjustment of the alignment target position for automatic alignment while directly confirming a transillumination observation image. Therefore, it is possible to easily perform fine adjustment of a measurement point with less influence of small involuntary eye movement of the fixing eye to be inspected. In addition, because it is not necessary to display the transillumination still image every time a measurement error occurs, the measurement time can be reduced, and hence it is possible to provide the ophthalmologic apparatus and ophthalmologic method having good operability.

Further features of the present invention will become apparent from the following description of exemplary embodiments with reference to the attached drawings.

BRIEF DESCRIPTION OF THE DRAWINGS

FIG. 5 is a system block diagram of the eye refractive power meter.

FIGS. 18A, 18B, 18C, 18D, 18E and 18F are diagrams relating to alignment of an ophthalmologic apparatus according to a sixth embodiment of the present invention, in which FIG. 18A is a diagram illustrating an anterior ocular segment image in a state of the transillumination observation, FIG. 18B is a diagram illustrating a luminance distribution on one central horizontal line in FIG. 18A, FIG. 18C is a diagram illustrating the anterior ocular segment image when fundus illumination light is turned off, FIG. 18D is a diagram illustrating a luminance distribution on one central horizontal line in FIG. 18C, FIG. 18E is a diagram illustrating an image obtained by subtracting the anterior ocular segment image of FIG. 18C from the anterior ocular segment image of FIG. 18A, and FIG. 18F is a diagram illustrating a luminance distribution on one central horizontal line in FIG. 18E.

DESCRIPTION OF THE EMBODIMENTS

Preferred embodiments of the present invention will now be described in detail in accordance with the accompanying drawings.

First Embodiment

The present invention is described in detail based on an embodiment illustrated with reference to the drawings.

Figure 1:
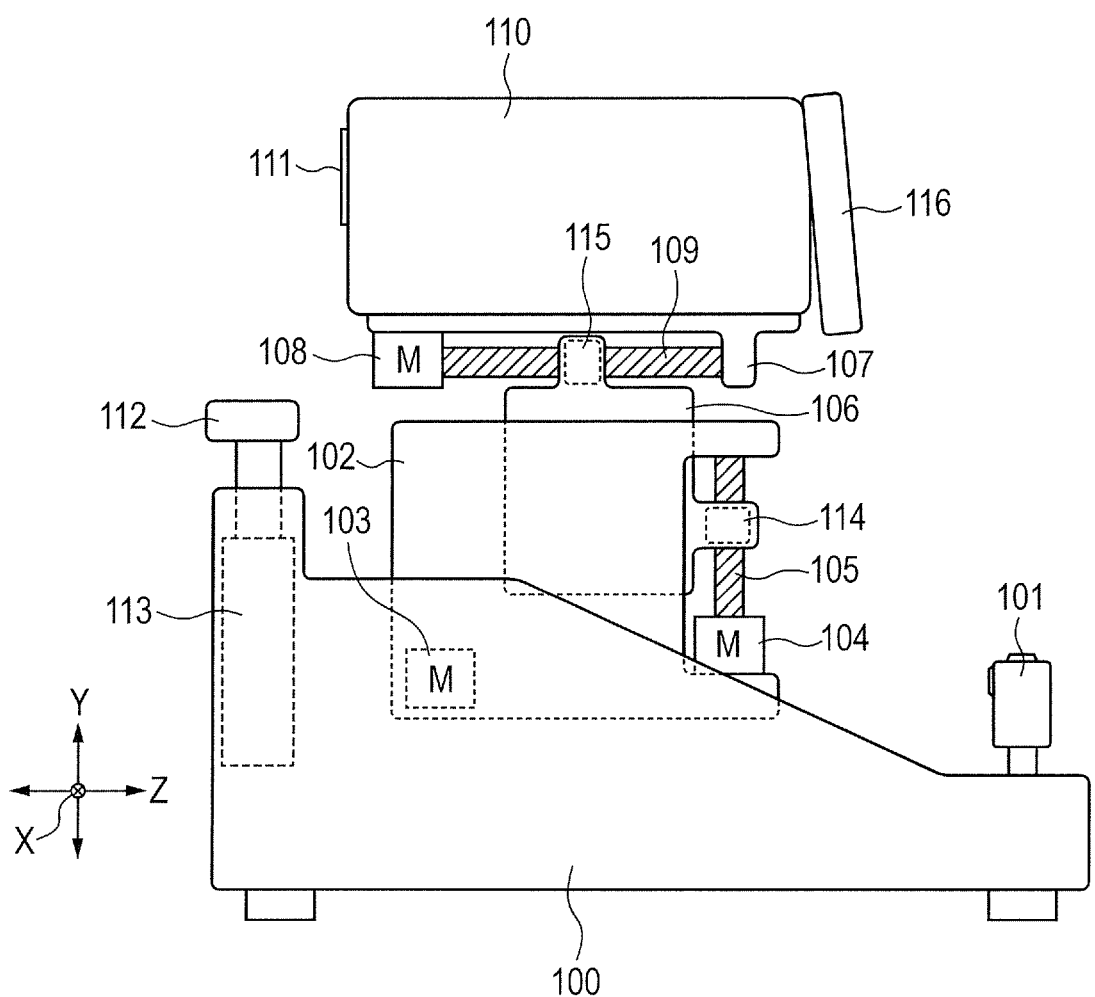
FIG. 1 is an appearance view of an eye refractive power meter.

FIG. 1 is a schematic structural view of an eye refractive power meter as an example of an ophthalmologic apparatus according to the present invention, which includes an acquiring portion for acquiring information on an eye to be inspected (for example, ocular refraction information, which is hereinafter referred to also as specific information of the eye to be inspected) by illuminating the eye to be inspected.

In the present invention, a measurement unit 110 as a measuring portion for measuring the eye to be inspected is supported by a base 100 through an intermediation of a frame 102, and drive mechanisms in X, Y, and Z axis directions, which are described later in detail. The frame 102 can move in left-right direction (hereinafter referred to as an X axis direction) with respect to the base 100. Note that, in the present invention, the measurement unit 110 corresponds to a measuring unit for measuring information of the eye to be inspected by illuminating the eye to be inspected, and a structure for driving the measurement unit 110 with respect to the base 100 as described later corresponds to a driving unit for driving the measuring unit.

A drive mechanism in the X axis direction is constituted of an X axis drive motor 103 fixed onto the base 100, a feed screw (not shown) connected to a motor output shaft, and a nut (not shown) fixed to the frame 102 so as to move along the feed screw in the X axis direction. When the motor 103 rotates, the frame 102 moves in the X axis direction via the feed screw and the nut. A frame 106 can move relative to the frame 102 in an up-down direction (hereinafter referred to as Y axis direction).

A drive mechanism in the Y axis direction is constituted of a Y axis drive motor 104 fixed onto the frame 102, a feed screw 105 connected to a motor output shaft, and a nut 114 fixed to the frame 106 so as to move along the feed screw in the Y axis direction.

When the motor 104 rotates, the frame 106 moves in the Y axis direction via the feed screw and the nut.

A frame 107 can move relative to the frame 106 in a front-back direction (hereinafter referred to as Z axis direction). A drive mechanism in the Z axis direction is constituted of a Z axis drive motor 108 fixed onto the frame 107, a feed screw 109 connected to a motor output shaft, and a nut 115 fixed to the frame 106 so as to move along the feed screw in the Z axis direction.

When the motor 108 rotates, the frame 107 moves in the Z axis direction via the feed screw 109 and the nut. The measurement unit 110 for measurement is fixed onto the frame 107.

The above-mentioned drive system for driving the measurement unit 110 in the X, Y, and Z axis directions with respect to the base 100 constitutes an electric driving unit for driving the measurement unit 110 in electric manner in the left-right direction, in the up-down direction, and in the front-back direction, as exemplified in the present invention.

A light source (not shown) for performing alignment and a light source unit 111 for measuring corneal curvature are disposed on an end portion of the measurement unit 110 on a subject side. The light source unit 111 may further include another light source for measuring corneal curvature.

In addition, the base 100 is provided with a joystick 101 as an operating member for aligning the measurement unit 110 with respect to an eye to be inspected E. By tilting the joystick when the measurement is performed, position control of the measurement unit 110 can be performed manually.

When refractive power measurement is performed, a subject places his or her chin on a chin rest 112 and presses his or her forehead to a forehead rest portion of a face rest frame (not shown) fixed to the base 100, and hence a position of the eye to be inspected can be fixed.

In addition, a position of the chin rest 112 can be adjusted in the Y axis direction in accordance with a size of a subject face by a chin rest drive mechanism 113.

On an end portion of the measurement unit 110 on an inspector side, there is disposed an LCD monitor 116 as a display member for observing the eye to be inspected E, which can display a measurement result and the like. Note that, the monitor for displaying a measurement result and the like may be an external monitor provided additionally to the measurement unit.

Figure 2:
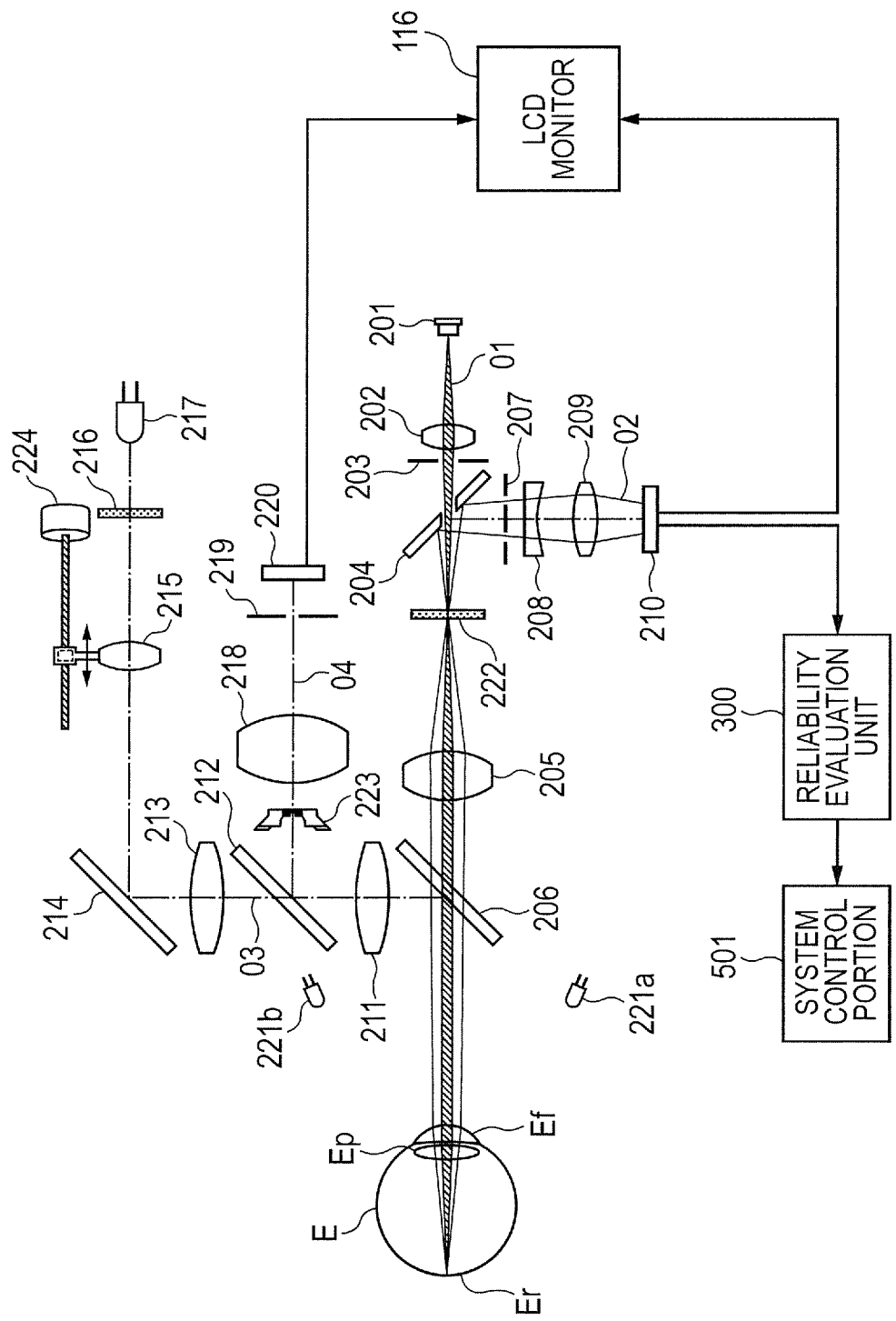
FIG. 2 is an arrangement diagram of an optical system of a measuring portion.

FIG. 2 is an arrangement diagram of an optical system disposed inside the measurement unit 110 as the acquiring portion for acquiring eye refractive power as the specific information of the eye to be inspected.

On an optical path 01 from an eye refractive power measurement light source 201 emitting light having a wavelength of 880 nm to the eye to be inspected E, there are disposed a lens 202, a aperture 203 substantially conjugate with a pupil Ep of the eye to be inspected E, a perforated mirror 204, a diffusion panel 222 that can be inserted and extracted, a lens 205, and a dichroic mirror 206 that totally reflects visible light from a side of the eye to be inspected E and partially reflects a light beam having a wavelength 880 nm, in this order. The eye refractive power measurement light source 201 functions as a fundus illumination light source for illuminating a fundus of the eye to be inspected in the present invention.

On an optical path 02 in the reflection direction of the perforated mirror 204, there are disposed an aperture 207 having a ring-like slit substantially conjugate with the pupil Ep, a light beam spectral prism 208, a lens 209, and an image pickup element 210, in this order.

When eye refractive power is measured, the translucent diffusion panel 222 is disposed outside the optical path by a diffusion panel insertion/extraction solenoid 510 (not shown, see FIG. 5). A light beam emitted from the measurement light source 201 is restricted by the aperture 203 and primarily forms an image on the lens 202 before the lens 205. Then, after passing through the lens 205 and the dichroic mirror 206, the light beam is projected to the pupil center of the eye to be inspected E.

The light beam forms an image on a fundus Er, and reflection light thereof passes through the pupil center and enters the lens 205 again. The entering beam passes through the lens 205 and then is reflected by a periphery of the perforated mirror 204.

The reflected beam is separated by pupil separation in the aperture 207 substantially conjugate with the pupil Ep of the eye to be inspected E and the beam spectral prism 208, and is projected as a ring image to a light receiving plane of the image pickup element 210.

When the eye to be inspected E is an emmetropic eye, this projected ring image becomes a predetermined circle. When the eye to be inspected E is a short-sighted eye, the projected circle becomes smaller than that in the emmetropic eye. When the eye to be inspected E is a long-sighted eye, the projected circle becomes larger than that in the emmetropic eye.

When the eye to be inspected E has astigmatism, the projected ring image becomes an ellipse in which an angle formed between a horizontal axis and a major axis or a minor axis of the ellipse is an astigmatism axis angle. Based on a coefficient of this ellipse, the refractive power is determined.

On the other hand, in the reflection direction of the dichroic mirror 206, there are disposed a fixation target projecting optical system and an alignment light receiving optical system used for both anterior ocular segment observation and alignment detection of the eye to be inspected.

On an optical path 03 of the fixation target projecting optical system, there are disposed a lens 211, a dichroic mirror 212, a lens 213, a reflection mirror 214, a lens 215, a fixation target 216, and a fixation target illumination light source 217 in the stated order.

When the fixation target direction is performed, a projection light beam from the turned-on fixation target illumination light source 217 illuminates the fixation target 216 from the backside, and is projected to the fundus Er of the eye to be inspected E via the lens 215, the reflection mirror 214, the lens 213, the dichroic mirror 212, and the lens 211.

Note that, the lens 215 can be moved in an optical axis direction by a fixation target direction motor 224 which performs diopter direction control so as to realize a fogged state of the eye to be inspected E.

The fixation target 216 is disposed at a predetermined reference position so as to perform preliminary measurement (first measurement). Then, based on the determined eye refractive power value, the lens 215 is moved to a position corresponding to the refractive power value by driving the fixation target direction motor 224 via a motor driving unit 514. Thus, the fixation target 216 is displayed on the eye to be inspected E at a refractivity corresponding to a refractivity of the eye to be inspected E. After that, the lens 215 is moved to the far side by a predetermined amount so that the fixation target 216 is fogged, and the measurement light source is turned on again so as to measure the refractive power. In this way, the measurement of the refractive power, the fogging by the fixation target 216, and the measurement of the refractive power are repeated so as to obtain a final measured value in which the refractive power is stabilized.

On an optical path 04 in the reflection direction of the dichroic mirror 212, there are disposed an alignment aperture 223 that can be inserted and extracted by an alignment prism aperture insertion/extraction solenoid 511 (not shown, see FIG. 5), a lens 218, and an image pickup element 220 in the stated order.

Further, anterior ocular segment illumination light sources (extraocular illumination light sources) 221a and 221b disposed in the vicinity of measuring portion of the apparatus or diagonally in front of an anterior ocular segment are illumination light sources for the anterior ocular segment of the eye to be inspected E which have a wavelength of approximately 780 nm. A beam from the anterior ocular segment image of the eye to be inspected E illuminated by the anterior ocular segment illumination light sources 221a and 221b forms an image on the image pickup element 220 via the anterior ocular segment reflection light optical path 04, which passes through the dichroic mirror 206, the lens 211, the dichroic mirror 212, and a center opening 223c of the alignment aperture.

Note that the anterior ocular segment illumination light sources 221a and 221b are illustrated in FIG. 2 to be arranged in the direction parallel to the drawing sheet (in a substantially vertical direction with respect to the eye to be inspected) for facilitating understanding, but actually the anterior ocular segment illumination light sources 221a and 221b are arranged in the direction perpendicular to the drawing sheet (in a substantially horizontal direction with respect to the eye to be inspected).

Figure 3:
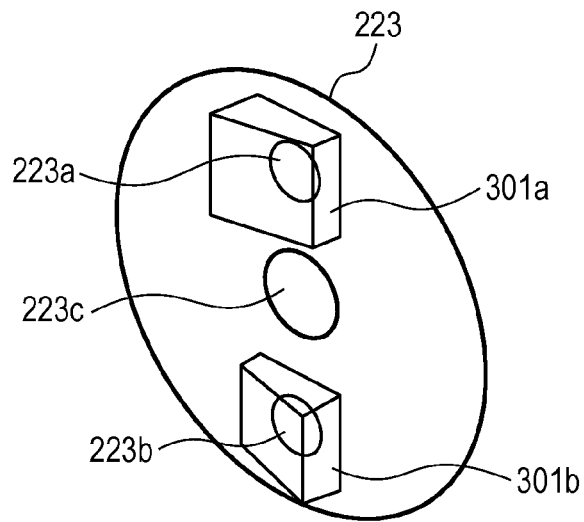
FIG. 3 is a perspective view of an alignment prism aperture.

FIG. 3 illustrates a shape of the alignment aperture 223, which may be disposed in the optical path in any direction. Three openings 223a, 223b, and 223c are formed in a disk-like diaphragm plate, and alignment prisms 301a and 301b for transmitting a light beam having a wavelength of approximately 880 nm are bonded to the openings 223a and 223b of both sides on the dichroic mirror 212 side.

By combining insertion/extraction of the diffusion panel 222 and the alignment aperture 223 described above, this apparatus can perform bright point detection for aligning the eye to be inspected and observation of a transillumination image.

In this apparatus, by combining insertion/extraction of the diffusion panel 222 and the alignment aperture 223 described above, it is possible to perform alignment using bright points for alignment and alignment using the transillumination moving image of the pupil of the eye to be inspected. In consideration that most human eyes to be inspected have the corneal apex decentered from the pupil center, the alignment using the transillumination moving image can be performed after performing the alignment using the bright points for alignment in this apparatus.

In addition, it is possible to change to the alignment by the transillumination moving image so as to perform the alignment by the transillumination moving image only in a case where an error occurs in acquiring the specific information of the eye to be inspected in the state where the alignment by the bright points for alignment has been performed (in a case where the specific information does not satisfy a predetermined condition).

When detecting the bright points for alignment, the alignment aperture 223 and the diffusion panel 222 are inserted in the optical path by the individual insertion/extraction mechanisms. The light source for alignment detection also works as the above-mentioned measurement light source 201 for measuring the eye refractive power. In addition, the position where the diffusion panel 222 is inserted is a primary image formation position by the projection lens 202 of the measurement light source 201 and is substantially a focal position of the lens 205. Thus, an image of the measurement light source 201 is temporarily formed on the diffusion panel 222, and the image becomes a secondary light source so that the lens 205 projects a thick collimated light beam toward the eye to be inspected E (this functions as an index light beam projecting unit for alignment with respect to the eye to be inspected).

This collimated light beam is reflected by a cornea Ef of the eye to be inspected, and the light beam passes through the center opening 223c of the alignment prism aperture and the alignment prisms 301a and 301b to be condensed by the lens 218. In addition, the light beam from the anterior ocular segment is condensed on a light receiving plane of the image pickup element 220 via the center opening 223c. The bright points condensed on the image pickup element 220 are superimposed on the above-mentioned anterior ocular segment image to form images as three alignment bright points in the pupil area. The light beam after passing through the alignment prism 301a is refracted in the right direction in FIG. 3, and the light beam after passing through the alignment prism 301b is refracted in the left direction in FIG. 3. In other words, the individual light beams are refracted to be arranged horizontally. Based on a positional relationship between these light beams after passing through the apertures, the alignment of the eye to be inspected E can be performed. The above-mentioned structure of the optical system for acquiring the anterior ocular segment image, on which the bright points are superimposed, constitutes an anterior ocular segment observing and image pickup unit for observing and picking up an image of the pupil area of the eye to be inspected in the present invention.

Figure 4A:
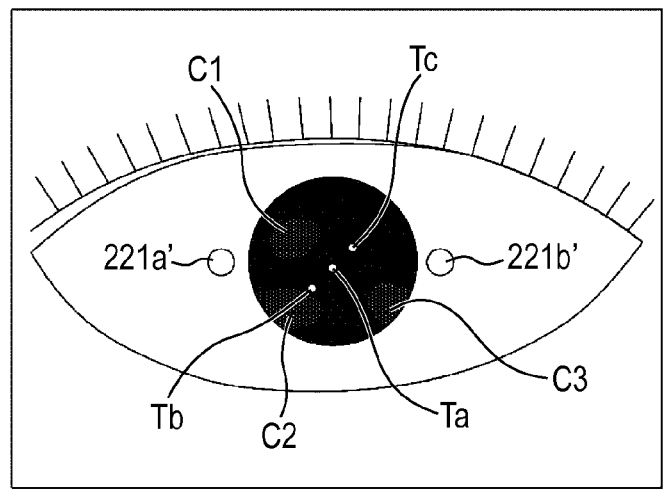
FIGS. 4A and 4B are comparative diagrams of display images in normal observation and in transillumination observation.

In this way, the bright points condensed on the image pickup element 220 are superimposed on the anterior ocular segment image, and specifically become the three alignment bright points within the pupil area as illustrated in FIG. 4A. Note that the light beam after passing through the alignment prism 301a in FIG. 3 is refracted in the left direction, while the light beam after passing through the alignment prism 301b is refracted in the right direction, and hence the three alignment bright points can be acquired. Here, when an alignment error occurs in the front-back direction, the three alignment bright points are positioned in a diagonal direction as illustrated in FIG. 4A.

Further, when the alignment is performed in the front-back direction, three alignment bright points are arranged in the left-right direction within the pupil area. Note that, individual apertures of the alignment prism aperture 223 are arranged to be aligned in the vertical direction on the optical path as illustrated in FIG. 3, but the individual apertures may be arranged to be aligned in the lateral direction. In this case, the light beam is refracted in the up-down direction by the individual prism. When the alignment is performed in the front-back direction, the three alignment bright points are arranged in the up-down direction.

Note that, a case where the condensed bright points are aligned in the horizontal direction is exemplified in this embodiment, but it is possible to dispose the alignment prism so that the refraction direction by the alignment prism becomes the up-down direction, so as to align the bright points in the vertical direction, and further to perform the alignment in an arbitrary direction.

In addition, when the alignment prism aperture 223 is inserted in a light receiving optical path, the light beam of the anterior ocular segment image forms an image on the light receiving plane of the image pickup element 220 via the center opening 223c. Therefore, compared with the case where the alignment prism aperture 223 is extracted from the optical path, light beams forming an image on the image pickup element 220 are decreased. Therefore, in this apparatus, in order to acquire the anterior ocular segment image having optimal luminance, light intensities of the anterior ocular segment illumination light sources 221 are changed in synchronization with insertion/extraction of the alignment prism aperture 223. When the alignment prism aperture 223 is inserted in the optical path, light intensity is increased. On the contrary, when the alignment prism aperture 223 is extracted from the optical path, it is preferred to decrease the light intensity of the anterior ocular segment illumination light source to be lower than that in the case where the alignment prism aperture 223 is inserted.

FIG. 4A illustrates an anterior ocular segment observation image displayed on the LCD monitor 116 when the alignment is performed. The eye to be inspected E and the vicinity thereof are illuminated by the extraocular illumination light sources 221a and 221b, and further on an iris of the eye to be inspected E, reflection images of the extraocular illumination light sources 221 are picked up as extraocular bright point images 221a' and 221b'.

In other words, images of the anterior ocular segment bright point images 221a' and 221b' are picked up by the image pickup element 220 as a light source image detecting unit and is displayed on the LCD monitor 116. In addition, images of the above-mentioned three alignment bright points within the pupil area (cornea bright points as the corneal reflex image of the index light beam) are picked up by the image pickup element 220 as a reflection image detecting unit and are displayed on the LCD monitor 116.

In addition, the cornea bright points obtained from the cornea reflection light beam of the measurement light reflected by the cornea Ef are divided by the openings 223a, 223b, and 223c of the alignment prism aperture 223 and the prisms 301a and 301b, which are picked up by the image pickup element 220 as index images Ta, Tb, and Tc. Symbols C1, C2, and C3 illustrated in FIGS. 4A and 4B denote opacified portions existing in the crystalline lens because of a disease such as cataract or the like. Because the pupil is dark in FIG. 4A, it is understood that it is difficult to determine positions and sizes of the opacified portions.

Next, there is described the combination of insertion/extraction of the diffusion panel 222 and the alignment prism aperture 223 when the transillumination image is observed. When the transillumination image is observed, the alignment prism aperture 223 and the diffusion panel 222 are extracted from the optical path by the individual insertion/extraction mechanisms. When the diffusion panel 222 is extracted from the optical path, the light beam from the measurement light source 201 is projected to the fundus Er without being diffused. The reflection light beam becomes the secondary light source from the fundus and can illuminate the pupil from inside of the eye to be inspected. Therefore, when the anterior ocular segment image observation is performed in a state where the alignment prism aperture 223 is extracted from the optical path 04, the pupil portion is illuminated brightly so that the anterior ocular segment image in a brightly illuminated state can be observed. In general, this state is called transillumination observation. Here, the transillumination observation can be performed also in the state where the alignment prism aperture 223 is inserted in the optical path.

However, when the alignment prism 223 is inserted in the optical path, images of three corneal reflex image bright points Ta, Tb, and Tc are formed and superimposed on the transillumination image as described above. Because the corneal reflex image is brighter than the transillumination image, there is a large demerit that a desired transillumination image cannot be acquired. Therefore, the alignment prism 223 is usually extracted from the optical path for performing the transillumination observation.

In the transillumination observation mode in which the pupil area illuminated by the reflection light beam from the fundus of the eye to be inspected (transillumination image) is observed, the measurement light source 201 is turned on, and the anterior ocular segment illumination light sources 221a and 221b are turned off. Then, the diffusion panel 222 and the alignment prism aperture 223 are extracted from the optical path. In other words, the measurement light source 201 projects light to the fundus Er, and the light beam reflected from the fundus Er illuminates the pupil area. Then, a part of the light beam in the pupil area is reflected by the dichroic mirror 206, passes through the lens 211, and is reflected by the dichroic mirror 212. Further, the lens 218 projects the pupil area to the image pickup element 220.

The pupil area projected to the image pickup element 220, which serves as a transillumination image acquiring unit for acquiring the transillumination image or a transillumination moving image acquiring unit for acquiring the transillumination moving image, is displayed on the LCD monitor 116 so that it is possible to observe whether or not the pupil area has an opacified portion. Note that, the display on the LCD monitor 116 serving as a display unit of the image obtained by the acquiring unit of the transillumination moving image and the like is performed by a module region functioning as a display control unit in a system control portion 501. Change from an eye refractive power information detection mode by an eye refractive power information detecting unit to the transillumination observation mode by a transillumination observing unit is automatically performed when a predetermined determination is performed as described in detail below. In this case, increase of light intensity of the measurement light source 201, extraction of the diffusion panel 222 and the alignment prism aperture 223 from the optical path, turning off of the anterior ocular segment illumination light sources 221a and 221b are performed specifically as the automatic change to the transillumination observation mode.

Figure 4B:
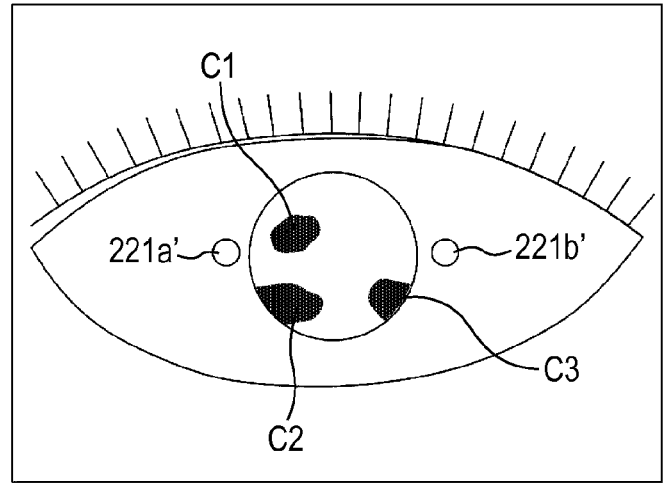

FIG. 4B illustrates an anterior ocular segment image displayed on the LCD monitor 116 when the transillumination observation is performed. When the transillumination observation is performed, the pupil area is illuminated from the backside by the fundus reflection light. Therefore, it is understood that opacified portions C inside the crystalline lens, which are hardly recognized in the ordinary anterior ocular segment observation image illustrated in FIG. 4A, can also be clearly distinguished. In this case, unlike the ordinary anterior ocular segment observation image (in which the pupil area is dark), the pupil area is observed as a bright portion. In this way, it is possible to extract the pupil as a bright portion (to extract an area having luminance of the transillumination image higher than a predetermined value as the pupil area). In addition, other portions than the pupil area can be observed in substantially the same luminance by light intensity adjustment of the extraocular illumination light sources 221. In addition, the reflection images 221a' and 221b' of the extraocular illumination light sources 221 can be observed in both the observation images of FIGS. 4A and 4B.

FIG. 5 is a system block diagram. The system control portion 501 which controls the entire system includes a program storage portion, a data storage portion for storing data for correcting the eye refractive power value, an input and output control portion for controlling input and output with various devices, and a calculation processing portion for calculating data obtained from various devices.

The system control portion 501 is connected to the joystick 101 for performing alignment of the measuring portion 110 with respect to the eye to be inspected E and for starting the measurement. On the joystick 101, there are disposed a tilt angle detection mechanism 502 for detecting the tilt angle when the joystick 101 is tilted in the front-back and right-left directions, an encoder input mechanism 503 when the joystick 101 is rotated, and a measurement start switch 504 activated when the measurement start switch is pressed. In addition, on an operation panel 505 (not shown) on the base 100, there are disposed a print switch, a chin rest up/down switch, and the like. When the switch is pressed, a signal is transmitted to the system control portion. After the alignment by the bright points for alignment and the alignment by the transillumination moving image of the pupil of the eye to be inspected, the anterior ocular segment image of the eye to be inspected E picked up by the image pickup element 220 is stored in a memory 508. In the alignment by the bright points for alignment, the system control portion 501 extracts the pupil image and the corneal reflex image of the eye to be inspected E from the image stored in the memory 508 so as to perform the alignment control. In the alignment by the transillumination moving image of the pupil of the eye to be inspected, the system control portion 501 extracts the pupil as a bright portion in the eye to be inspected E from the image stored in the memory 508 so as to perform the alignment control. In this way, the pupil area is extracted by using the transillumination moving image, and hence the lashes can be detected as a dark portion, while the pupil area can be detected as a bright portion. Thus, occurrence of a detection error can be prevented.

The anterior ocular segment image of the eye to be inspected E picked up by the image pickup element 220 is stored in the memory 508. Note that, at the time of storing the anterior ocular segment image, it is desired to simultaneously store data on operation performed at the time of image pickup operation, such as an alignment position and an offset amount of the alignment position described below. A pupil and corneal reflex image of the eye to be inspected E is extracted from the image stored in the memory 508, and the alignment detection is performed. In addition, the anterior ocular segment image of the eye to be inspected E picked up by the image pickup element 220 is combined with data of characters and graphics, and then the anterior ocular segment image, a measurement value, and the like are displayed on the LCD monitor 116. Further in this case, it is preferred that stored data such as the above-mentioned alignment position be displayed at the same time.

The ring image for calculating the eye refractive power, which is picked up by the image pickup element 210, is stored in the memory 508.

Then, the measured value of the eye refractive power is combined with the anterior ocular segment image of the eye to be inspected E picked up by the image pickup element 220, character and graphic data, and the like, so as to be displayed on the LCD monitor 116. The measurement light source 201, the anterior ocular segment illumination light sources 221a and 221b, and the fixation target light source 217 are controlled by instructions from the system control portion 501 via a light source drive circuit 513 about turning on and off and changing intensity of light.

The diffusion panel insertion/extraction solenoid 510 and the alignment prism aperture insertion/extraction solenoid 511 are driven and controlled by instructions from the system control portion 501 via a solenoid driving unit 509. In addition, the X axis drive motor 103, the Y axis drive motor 104, the Z axis drive motor 108, the chin rest drive mechanism 113, and the fixation target direction motor 224 are driven by instructions from the system control portion 501 via the motor drive circuit 514.

The measurement light source 201, the anterior ocular segment illumination light sources 221a and 221b, and the fixation target light source 217 are controlled by instructions from the system control portion 501 via a light source drive circuit 513 about turning on and off and changing intensity of light.

Next, operations of the system control portion 501 from the automatic alignment control until the eye refractive power measurement are described.

The inspector operates the joystick 101 so as to move the measurement unit 110 until a part of the pupil of the eye to be inspected is displayed on the LCD monitor 116. After a part of the pupil is displayed on the LCD monitor 116, the measurement start switch 504 is pressed so that the automatic alignment control is started by the system control portion 501. This automatic alignment control is performed by a module region functioning as an automatic alignment unit for automatically performing the alignment between the measurement unit 110 and the eye to be inspected in the system control portion 501.

The system control portion 501 analyzes the anterior ocular segment image acquired by the image pickup element 220 by a module region functioning as a pupil center or pupil position detecting unit so as to detect the pupil of the eye to be inspected. The pupil position detecting unit detects a pupil position from the transillumination image of the anterior ocular segment of the pupil area illuminated by diffused light obtained from the fundus of the eye to be inspected illuminated by the fundus illumination light source. When the pupil is detected, X and Y axis motor control is performed by the motor driving unit 514 in the direction in which a pupil center axis and an optical axis 01 of the measurement unit 110 match with each other. When the pupil center axis of the eye to be inspected E is substantially matched with the optical axis 01 of the measurement unit 110, the light sources images 221a' and 221b' of the extraocular illumination light sources 221 appear on the anterior ocular segment. Therefore, the system control portion 501 performs X, Y, and Z axis motor control so that the reflection light images 221a' and 221b' have predetermined positions and sizes. When the reflection light images 221a' and 221b' have predetermined positions and sizes, the above-mentioned bright points Ta, Tb, and Tc for alignment detection appear in the pupil area.

When the three bright points Ta, Tb, and Tc are detected, the system control portion 501 controls the motor drive circuit 514 so as to drive the measuring portion 110 in the up-down and left-right directions so that the center bright point Ta is matched with the optical axis 01 of the measuring portion 110. Next, the system control portion 501 drives the measuring portion 110 further in the front-back direction so that the bright points Tb and Tc are aligned with respect to the bright point Ta in the vertical direction. Then, the alignment is completed in a state where the three cornea bright points Ta, Tb, and Tc are aligned in the up-down direction.

Next, in order to measure the eye refractive power, the system control portion 501 extracts the diffusion panel 222, which was inserted in the optical path 01 for the automatic alignment, from the optical path 01. Light intensity of the measurement light source 201 is adjusted, and the measurement beam is projected to the fundus Er of the eye to be inspected E.

The reflection light from the fundus propagates along the optical path 02 and is received by the image pickup element 210. The picked-up fundus image is projected in a ring shape by the refractive power of the eye to be inspected and by the ring aperture 207. This ring image is stored in the memory 508. Next, barycentric coordinates of the ring image stored in the memory 508 are calculated, and an ellipse equation is determined by a well-known method. A long diameter, a short diameter, and a tilt angle of the major axis of the determined ellipse are calculated so that the eye refractive power of the eye to be inspected E is calculated. Note that, the determined eye refractive power value corresponding to the long and short diameters of the ellipse, and a relationship between an angle of an ellipse axis on a light receiving plane of the image pickup element 210 and an astigmatic axis are corrected in advance in a manufacturing process of the apparatus.

On the other hand, in the reflection direction of the dichroic mirror 206, there are disposed the fixation target projecting optical system and the alignment light receiving optical system used for both anterior ocular segment observation (rough alignment) described later and alignment detection (fine alignment) of the eye to be inspected. On the optical path 03 of the fixation target projecting optical system, there are disposed the lens 211, the dichroic mirror 212, the lens 213, the reflection mirror 214, the lens 215, the fixation target 216, and the fixation target illumination light source 217 in the stated order.

When the fixation target direction is performed, the projection light beam from the turned-on fixation target illumination light source 217 illuminates the fixation target 216 from the backside, and is projected to the fundus Er of the eye to be inspected E via the lens 215, the reflection mirror 214, the lens 213, the dichroic mirror 212, and the lens 211.

When the eye refractive power is obtained, the motor driving unit 514 moves the lens 215 by the fixation target direction motor 224 to a position corresponding to the refractive power value of the eye to be inspected E.

After that, the lens 215 is moved to the far side by a predetermined amount so that the fixation target 216 is fogged, and the measurement light source is turned on again so as to measure refractive power.

In this way, the procedure of measurement of the refractive power, fogging by the fixation target 216, and measurement of refractive power are repeated until the measured value is stabilized, and hence a true value of the eye refractive power can be obtained.

Usually, in this way, the measurement of eye refractive power is finished. However, as to an eye to be inspected having opacity in the crystalline lens, there is a case where the projection light beam from the measurement light source 201 does not reach the fundus Er because of the opacity or a case where a part of the reflection light beam is blocked by the opacity, and hence a desired ring image cannot be picked up by the image pickup element 210 so that the measurement itself cannot be performed.

Figure 6A:
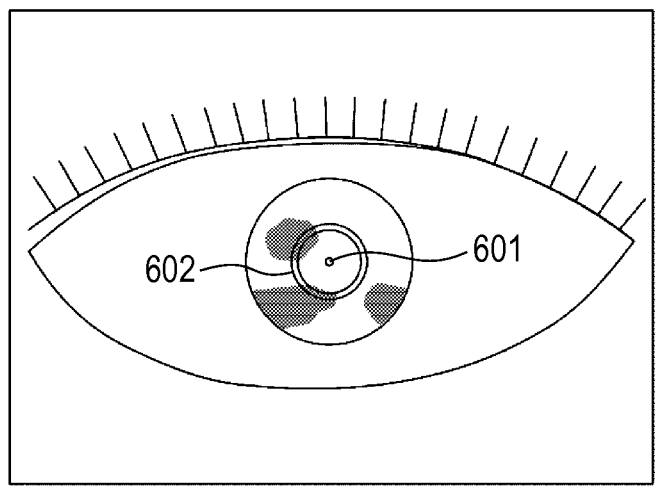
FIG. 6A illustrates an example of a transillumination image.
Figure 6B:
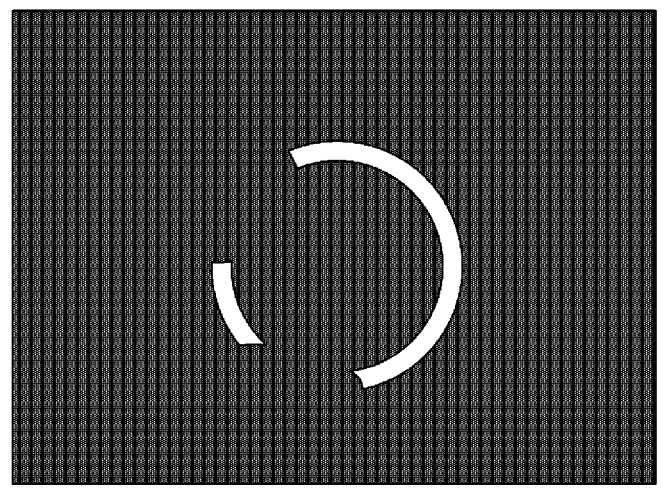
FIG. 6B illustrates an example of a ring image, when a crystalline lens has opacified portions.

In addition, FIG. 6A is a schematic diagram illustrating places through which measurement light 601 projected to the fundus and a ring light beam 602 used for measurement pass. In reality, because the measurement light 601 is reflected by the fundus Er in all directions and illuminates the entire pupil from the backside, the ring image as illustrated in FIG. 6A is not obtained. The reflection light from the pupil is separated by the aperture 207 through pupil separation so as to be a ring image, and is projected to the light receiving plane of the image pickup element 210. FIG. 6B illustrates a ring image formed on the image pickup element 210 when the ring light beam 602 is partially blocked by the opacity.

In the eye to be inspected having opacity, even when the projection light beam reaches the fundus Er, the reflection light may be blocked by the opacity as illustrated in FIG. 6A. Then, the ring image 602 for calculating refractive power is partially lost or blurred, and hence only a measurement result with low reliability is obtained.

Therefore, as for the eye to be inspected having opacity because of a disease such as cataract or the like, it is necessary to perform the eye refractive power measurement while avoiding opacified positions in the transillumination observation state.

An ophthalmologic measuring method according to an embodiment of the present invention is described below, which is performed by using the ophthalmologic apparatus having the structure described above.

Figure 7:
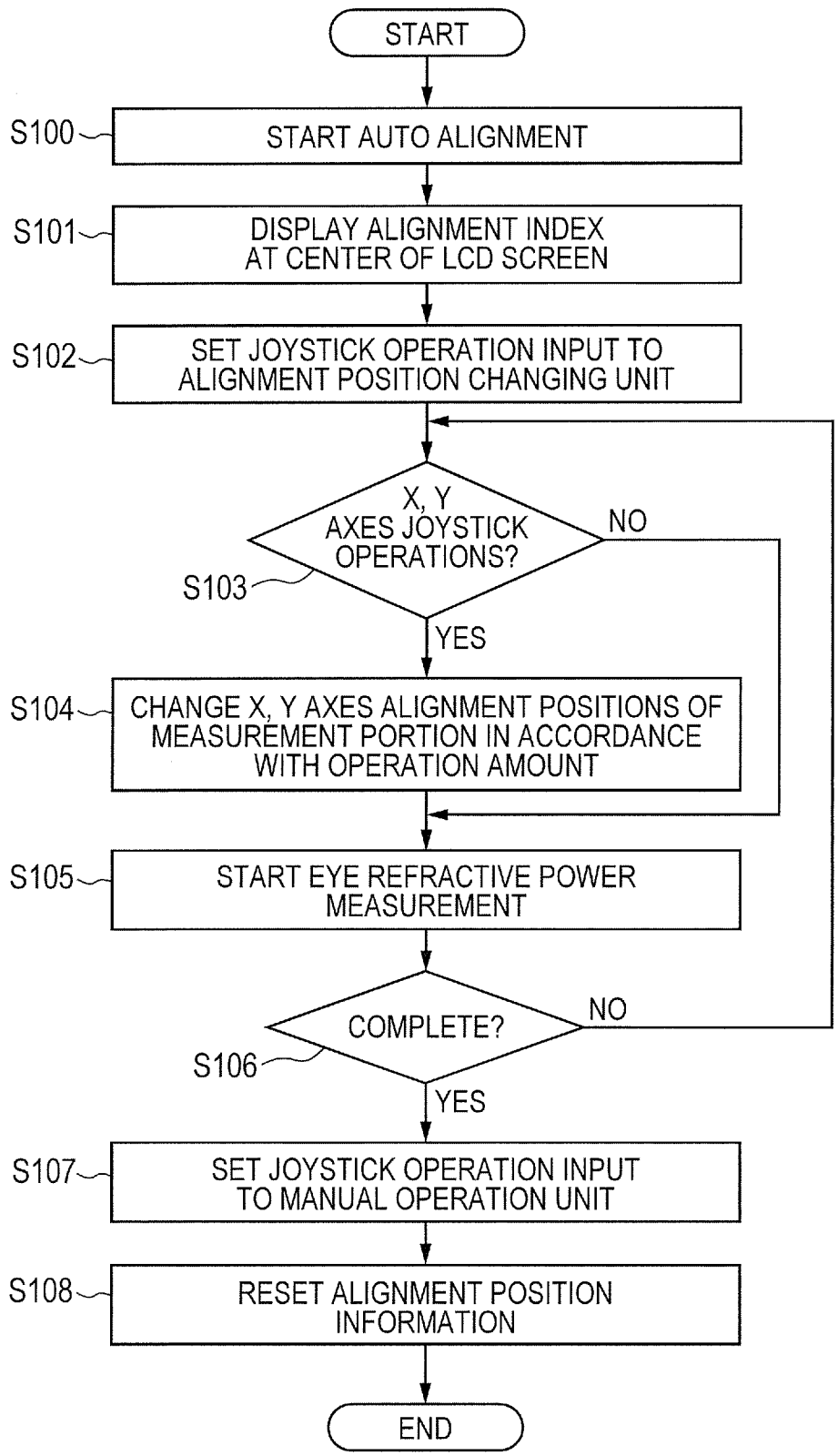
FIG. 7 is a flowchart illustrating a first embodiment of the present invention.

Here, characteristic control of the present invention in the transillumination observation is described in detail below with reference to a flowchart of FIG. 7.

When the change to the transillumination observation is instructed by the inspector, the system control portion 501 starts the automatic alignment of the transillumination observation in Step S100. Here, the automatic alignment in the transillumination observation does not primarily relate to the present invention, and hence is briefly described with an example below.

First, the system control portion 501 starts to detect the pupil in order to perform the alignment in the X and Y axes. As already described above, the pupil portion in the transillumination observation is detected as a bright area illuminated by the reflection measurement light from the fundus Er. In general, the pupil in the transillumination observation is sufficiently brighter than the lashes or the iris, and hence can be easily detected. Next, circle approximation of the detected pupil is performed so as to calculate the pupil center position. When the pupil center is calculated, the system control portion 501 performs the alignment in the X and Y axis directions so that the optical axis 01 of the measurement unit 110 matches with the pupil center.

Next, the alignment in the Z axis direction is described. The alignment in the Z axis direction is performed by using the extraocular illumination bright points $221a'$ and $221b'$. As illustrated in FIGS. 4A and 4B, the extraocular illumination bright points $221a'$ and $221b'$ are displayed in both the normal observation and the transillumination observation. Therefore, the system control portion 501 stores in the memory 508 the anterior ocular segment image and information such as the position and size of the extraocular illumination reflection bright points $221a'$ and $221b'$ when the alignment by the three bright points Ta, Tb, and Tc is finished. When the transillumination observation is performed, it is possible to perform the alignment in the Z axis direction based on information of the extraocular illumination reflection bright points $221a'$ and $221b'$ stored in the memory 508. In addition, the Z axis alignment is performed by using the extraocular illumination reflection bright point $221'$ in this embodiment, but it is possible to use an additional light source for the Z axis alignment and another optical system such as a light receiving sensor.

In Step S101, the system control portion 501 displays an alignment index as the character 601 on a screen display portion of the LCD monitor 116. This index indicates the optical axis 01 of the measurement unit 110, and the index in the automatic alignment matches with the pupil center when the transillumination observation is started. In addition, it is possible that the alignment index indicates not only the optical axis 01 of the measurement unit 110 but also the virtual ring image 602 for the eye refractive power measurement as illustrated in FIG. 6A by numeral 602.

In Step S102, the system control portion 501 switches the control method for an input from the joystick 101 from a manual control unit to an alignment position changing unit.

When the input of the joystick 101 is set to the manual control unit, if the joystick 101 is tilted in the front-back direction or in the left-right direction, the measurement unit 110 moves in the front-back direction (Z axis direction) or in the left-right direction (X axis direction) in accordance with the tilt angle. Further, the measurement unit 110 moves in the up-down direction (Y axis direction) when an encoder disposed in a coaxial manner is rotated in the left-right direction. In addition, the movement amount corresponds to the input of the joystick 101 on a one-to-one basis.

On the other hand, after changing to the control by the alignment position changing unit that is characteristic control of this embodiment, the input from the joystick 101 indicates an offset amount between the optical axis 01 of the apparatus and the pupil center (a shift amount or a desired movement amount of the alignment position). In this case, only the tilt operation in the left-right direction and the up/down instruction by the encoder can be input by the joystick 101.

When the inspector operates the joystick 101 in Step S103, in Step S104, the system control portion 501 calculates a movement amount from the optical axis center position in accordance with the input amount while maintaining the automatically aligned state, and changes an alignment target position. In other words, the reference position is initially set as the alignment target position for alignment between the eye to be inspected and the measurement unit 110, and this reference position is changed based on the moving image displayed on the display unit. This change is performed by a module region which functions as the changing unit in the system control portion 501. When the alignment target position is changed, the apparatus starts to follow a new alignment position. Because a follow speed of the apparatus is sufficiently faster than human perception, it is observed as if the anterior ocular segment image moves in the direction opposite to the operation direction of the joystick 101 when the above-mentioned control is performed.

After changing the alignment position to an arbitrary position, when the measurement start switch is pressed, the system control portion 501 performs the above-mentioned follow operation having the set offset amount effective therefor, and in Step S105, starts the eye refractive power measurement. In other words, the system control portion 501 as a control unit starts to control the driving unit to perform the alignment by using the changed reference position.

This change of the alignment position, in which the center position of the optical axis of the measurement unit 110 is offset or moved to an arbitrary position with respect to the pupil center, is performed by a module region which functions as the alignment position changing unit in the system control portion 501. This alignment of the center position of the optical axis is performed when the system control portion 501 drives the measurement unit 110 based on the reference position changed previously.

The measurement of information on the eye to be inspected by using the measurement unit 110 is performed a plurality of times, and alignment operation is performed based on the reference position changed in accordance with the measurement. In this embodiment, in Step S106, the system control portion 501 determines a measurement completion condition and repeatedly performs the control of Steps S103 to S105 until a desired measurement result is obtained or the number of measurement times is satisfied.

When the measurement condition is satisfied, in Step S107, the input of the joystick 101 is reset to the manual operation unit from the alignment position changing unit, and in Step S108, the input information from the alignment position changing unit is reset. Accordingly, and the automatic alignment transillumination observation is ended. In this embodiment, it is possible to perform manual operation of the driving unit by using the operation unit (not shown) as described above. In addition, the system control portion 501 described above can also perform offset of the optical axis of the measurement unit 110 by using the driving unit.

By this control switching, the inspector can change the automatic alignment target position while performing the transillumination observation, so as to perform the eye refractive power measurement while avoiding opacified portions. The present invention has a feature in being tolerant to small involuntary eye movement of the eye to be inspected, compared with the conventional control in which an offset amount is set in the transillumination still image, and the alignment position is changed in the normal observation. Further, there is no state transition between the still image display and the normal observation screen even in a case where the measurement is performed in a plurality of points while avoiding opacity positions. Therefore, it is easy to perform the measurement.

Finally, a specific operation of the apparatus in response to an input by the alignment position changing unit is described with reference to FIGS. 8A and 8B.

Figure 8A:
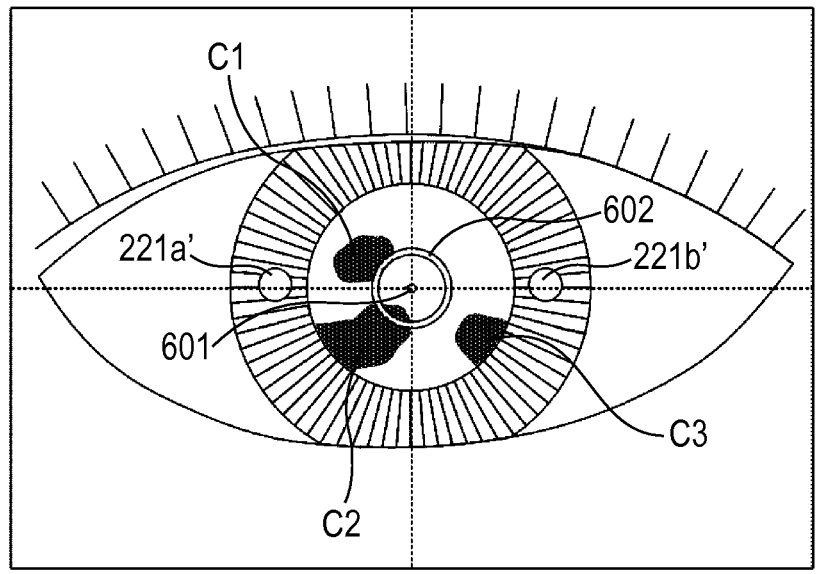
FIGS. 8A and 8B illustrate an example of moving an alignment position when the first embodiment is implemented.

When changing to the transillumination observation, the optical axis 01 of the apparatus is matched with the pupil center axis as illustrated in FIG. 8A. With respect to movement of the eye to be inspected, the X and Y axis automatic alignment is performed while maintaining a working distance to be constant by the extraocular illumination reflection bright points 221a' and 221b'.

Note that, this working distance is detected in advance by a working distance detecting unit which detects a distance in the optical axis between the measurement unit 110 and the eye to be inspected by using the above-mentioned bright points. The system control portion 501 performs this detection operation in a module region which functions as the working distance detecting unit. When the automatic alignment is performed, the alignment operation is performed by taking a detection result from the detection operation into consideration.

Figure 8B:
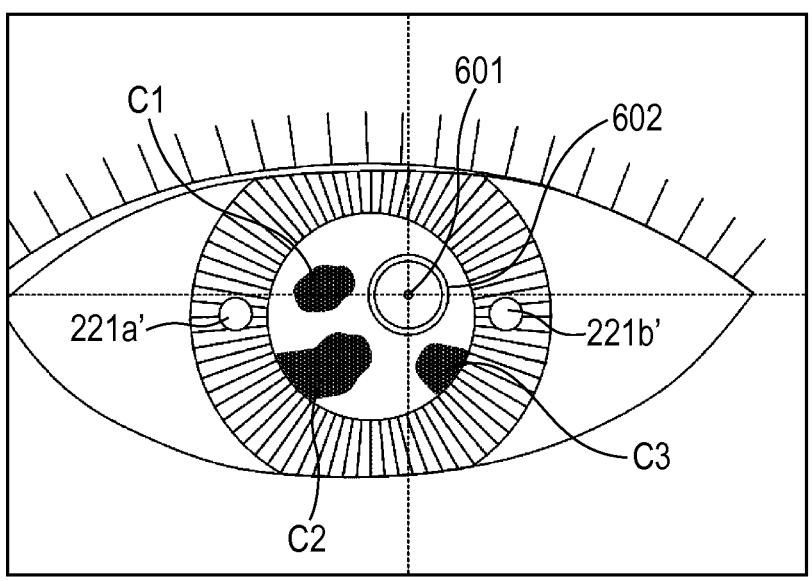

Symbols C1 to C3 in FIGS. 8A and 8B represent opacified portions in the crystalline lens, which exist on the ring image 602. In order to avoid the opacified portions, as easily understood, it is sufficient that the center position of the automatic alignment exist on the upper right portion of the eye to be inspected. Therefore, the inspector can change the center position of the alignment to a desired position by tilting the joystick 101 in the right direction and by rotating the encoder.

FIG. 8B illustrates the automatically aligned state after the alignment position is changed. Because there is no opacified portion overlapping on the optical axis center image 601 and the ring image 602, appropriate measurement can be performed. Here, the extraocular illumination reflection bright points 221a' and 221b' can be confirmed as bright points on the iris similarly to the case of FIG. 8A, and the alignment in the Z axis direction can be performed also in the offset state. Note that, there is a risk that when the operator does not confirm the original alignment center in the display state illustrated in FIG. 8B, the operator cannot determine whether or not the image is an image after the alignment position is changed. Therefore, in the display state of FIG. 8B, it is desired to display the original alignment center and the offset amount at the same time. As described above, the data related to the offset amount is preferred to be stored together with the image, and it is desired to display also the stored data when the image is displayed. Thus, the description of the control method of the first embodiment is finished.

Second Embodiment

The present invention is described based on another embodiment illustrated with reference to the drawings. Note that, in the embodiment described below, a basic structure of the apparatus is the same, and hence detailed description of the structure is omitted.

In addition, description until the start of the transillumination observation is omitted because it is the same as that of the first embodiment.

Figure 9:
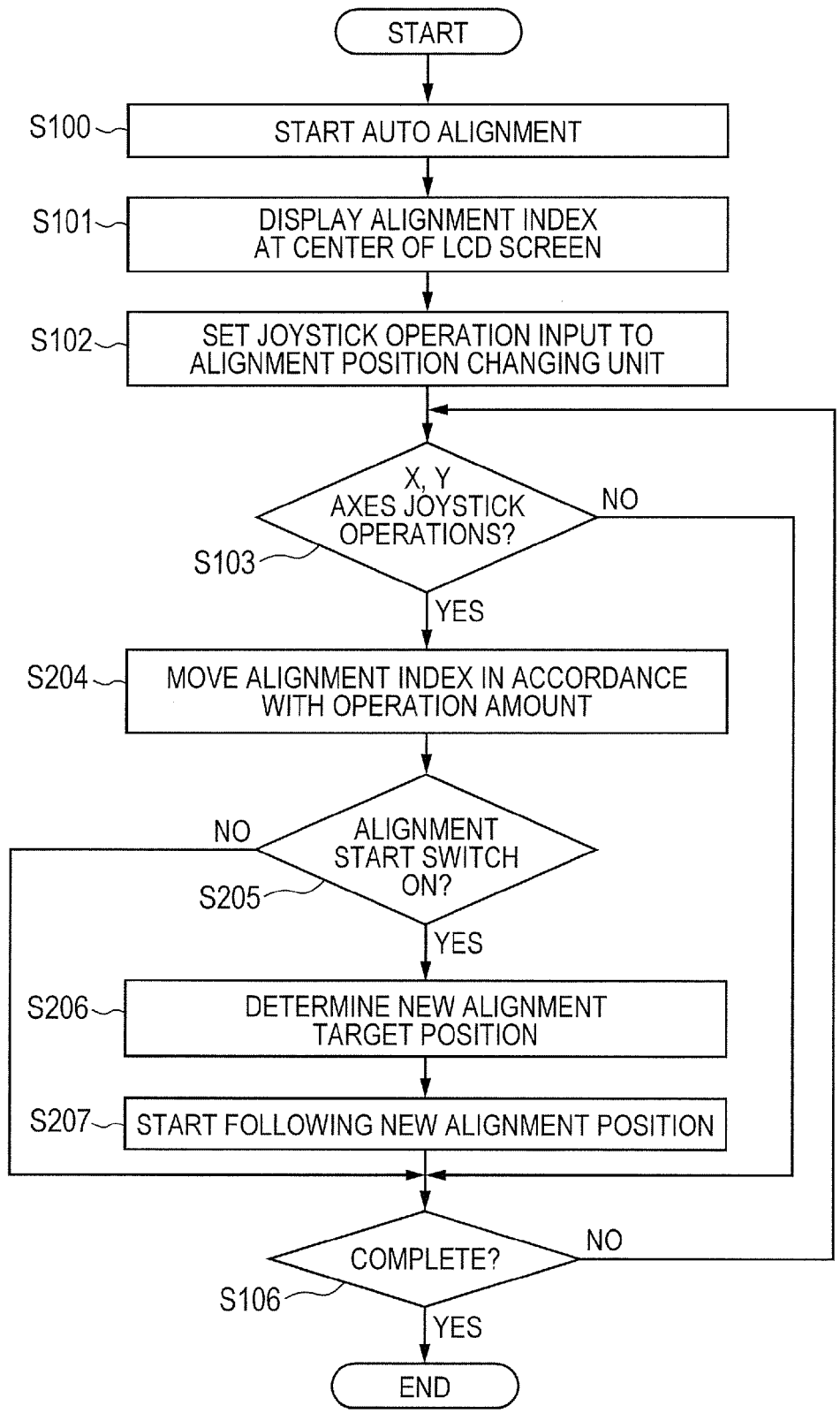
FIG. 9 is a flowchart illustrating a second embodiment of the present invention.

The control of the second embodiment is described with reference to a flowchart of FIG. 9 and an index movement diagram of FIG. 10. The control of Steps S100 to S103 is the same as that of the first embodiment.

Figure 10:
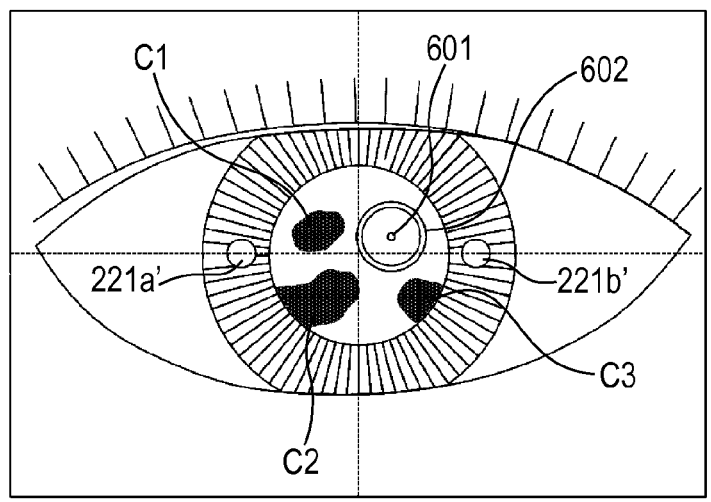
FIG. 10 illustrates an example of moving the alignment position when the second embodiment is implemented.

When the joystick 101 is operated in Step S103, in Step S204, the system control portion 501 moves the alignment indexes 601 and 602 on the LCD monitor 116 in accordance with the operation amount as illustrated in FIG. 10. In this case, the alignment position of the apparatus maintains the state before the indexes are moved. At the time immediately after the transillumination observation is started, the automatic alignment control is being performed so that the optical axis 01 of the measurement unit 110 matches with the pupil center.

When the alignment indexes are moved by operation of the joystick 110 to positions at which the alignment indexes are not blocked by the opacified portions or to positions desired by the inspector for the measurement, an alignment start switch is pressed. In Step S205, the position at which the alignment start switch is pressed is determined as a new alignment target position. In Step S206, the system control portion starts the alignment with respect to the new alignment target position (Step S207).

The above-mentioned control is performed until the measurement is completed. The process when the measurement is completed and the measurement completion condition are the same as those in the first embodiment, and hence description thereof is omitted.

Thus, the description of the control method of the second embodiment is finished.

First Modified Example

The automatic alignment control is performed automatically at the timing of changing to the transillumination observation in the embodiments of the present invention. This is performed for the purpose of providing the inspector with operational continuity in changing from the normal observation to the transillumination observation. However, it is possible to adopt such a structure of the apparatus that the inspector selects the automatic alignment control or the manual alignment control as an operation in the transillumination observation.

Further, after finishing the measurement, in Step S106, the control method for the input of the joystick 110 is switched from the alignment position changing unit to the manual operation unit. This timing can be arbitrarily changed. For instance, the timing includes a case of switching between left and right eyes before the measurement is completed, a case where the subject has been switched, and a case where the mode for acquiring the anterior ocular segment transillumination image is switched to the mode for acquiring another image or a measurement mode for performing other measurement. In addition, in this case, the operation of the alignment position changing unit may be automatically switched to an operation of the automatic alignment unit.

In addition, in the above-mentioned embodiments, the eye refractive power meter is described, but the present invention can be similarly applied to other ophthalmologic apparatus such as a fundus camera, a fundus blood flow meter, or a fundus tomographic imaging apparatus (OCT) using optical interference of a near infrared laser.

Third Embodiment

Next, a third embodiment of the present invention is described.

Note that, prior to detailed description of the embodiment, a measurement error considered in the present invention is described first.

(Measurement Error and Transillumination Observation)

When a measurement error occurs, it is possible to perform control so that the eye refractive power information measurement mode is automatically changed to the transillumination observation mode (in which the transillumination image is acquired as a moving image) regardless of a type of the measurement error. The present invention includes this case. With respect to this case, in the embodiment described below, there is provided a reliability evaluation unit having a function of evaluating reliability of the measurement result as well as a function of a determination unit for determining a type of the measurement error.

Further, based on a determination result about a type of the measurement error, it is determined whether or not to control the transillumination image acquiring unit to acquire the transillumination image as a moving image. Then, only in the case of the type requiring the transillumination observation, the mode is automatically changed to the transillumination observation mode (in which the transillumination image is acquired as a moving image). In this case, it is preferred to display a display form indicating a type of the measurement error on the display portion. When the display on the display portion is switched to a moving image of the transillumination image, the user can know the reason of the switching. Therefore, convenience is improved. In this case, it is sufficient that the user be able to know the reason when the display is switched. Therefore, it is possible that the display form indicating a type of the measurement error disappears after a predetermined period of time elapses.

On the other hand, when the type is not the type requiring the transillumination observation, control is performed not to automatically change the mode to the transillumination observation mode (in which the transillumination image is acquired as a moving image) but to measure the eye refractive power information again.

In other words, when it is sufficient that the measurement be performed again as in a case where a foreign matter adheres to the eye to be inspected or a case where a blink occurs so that a refractive power measurement error occurs as described below, the mode is not automatically switched to the transillumination observation mode, but the eye refractive power information is measured again.

(Reliability Evaluation and Type of Measurement Error)

(1) Measurement Error in Case of Low Reliability

Usually, the measurement of the eye refractive power is completed in this way. However, in the case described below, the reflection light from the fundus of the eye to be inspected cannot be picked up as an appropriate ring image by the image pickup element 210, and hence a reliability evaluation unit 300 determines a measurement error as a low reliability case. Then, the reliability evaluation unit 300 determines reliability of the eye refractive power information and determines a measurement error (acquisition error) when the reliability is low (when the reliability of a result of acquiring the specific information is below a predetermined value), and further determines a type of the measurement error.

(2) Measurement Error Due to Crystalline Lens Opacity

Figure 11A:
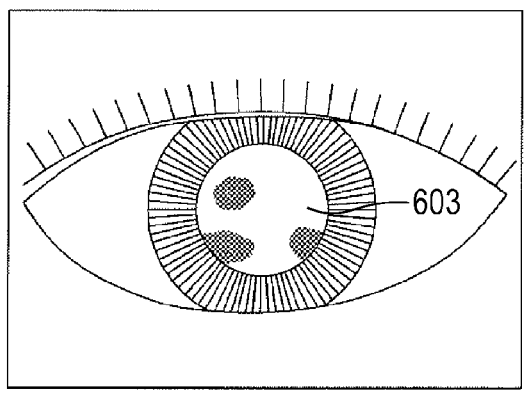
FIG. 11A illustrates a transillumination image.
Figure 11B:
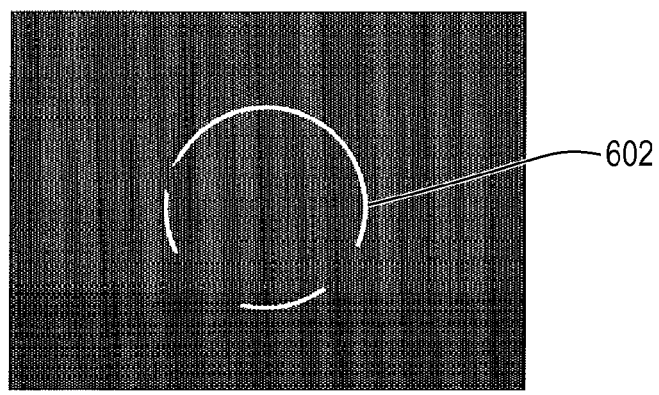
FIG. 11B illustrates a picked-up ring image, when a crystalline lens has opacified portions.

As to an eye to be inspected 603 having crystalline lens opacity as illustrated in FIG. 11A, even when the projection light beam reaches the fundus Er, the reflection light is blocked by the opacity. Consequently, as illustrated in FIG. 11B, the ring image 602 for calculating the refractive power is partially lost or blurred, and hence only a measurement result with low reliability is obtained. In this case, a determination criterion for the reliability evaluation unit 300 to determine a measurement error is presence or absence of a state where the image formed with the reflection light beam from the fundus by the eye refractive power information measuring unit is partially lost or blurred. Then, when the reliability evaluation unit 300 determines that the type of the measurement error is a measurement error due to the crystalline lens opacity, the change (automatic change) to the transillumination observation mode is performed.

In order to quickly change to the transillumination observation in an automatic manner, it is possible to utilize the fact that the alignment is completed in the eye refractive power measurement. In other words, unlike a case of the change that requires time (including manual alignment), it is not necessary to perform the alignment again (it is difficult to perform the alignment in the transillumination observation), and therefore it is a very superior form in a practical use.

(3) Measurement Error Due to Adhesion of Foreign Matter (Gum or the Like) to the Eye to be Inspected When a foreign matter adheres to the eye to be inspected, the measurement light beam cannot be picked up as an image. However, when a plurality of times of the measurement (main measurement after the preliminary measurement) are tried, the foreign matter is extracted by blinking, and hence the measurement light beam can be picked up as an image. In this case, a determination criterion for the reliability evaluation unit 300 to determine a measurement error is presence or absence of a state where the measurement light beam is not picked up as an image. Then, when the reliability evaluation unit 300 determines that a type of the measurement error is the measurement error caused by a foreign matter adhering to the eye to be inspected, the change (automatic change) to the transillumination observation mode is not performed.

(4) Measurement Error Due to Blinking

When blinking occurs in the measurement, the measurement light beam cannot be picked up as an image. However, when the measurement is tried again, the measurement light beam can be picked up as an image. In this case, a determination criterion for the reliability evaluation unit 300 to determine a measurement error is presence or absence of a state where the measurement light beam is not picked up as an image. Here, there is added a structure for picking up the anterior ocular segment image simultaneously when picking up the ring image for measuring the eye refractive power so as to determine whether or not blinking has occurred based on the anterior ocular segment image. Then, when the reliability evaluation unit 300 determines a type of the measurement error to be a measurement error caused by blinking, the change (automatic change) to the transillumination observation mode is not performed.

(Measurement Flow)

Figure 12:
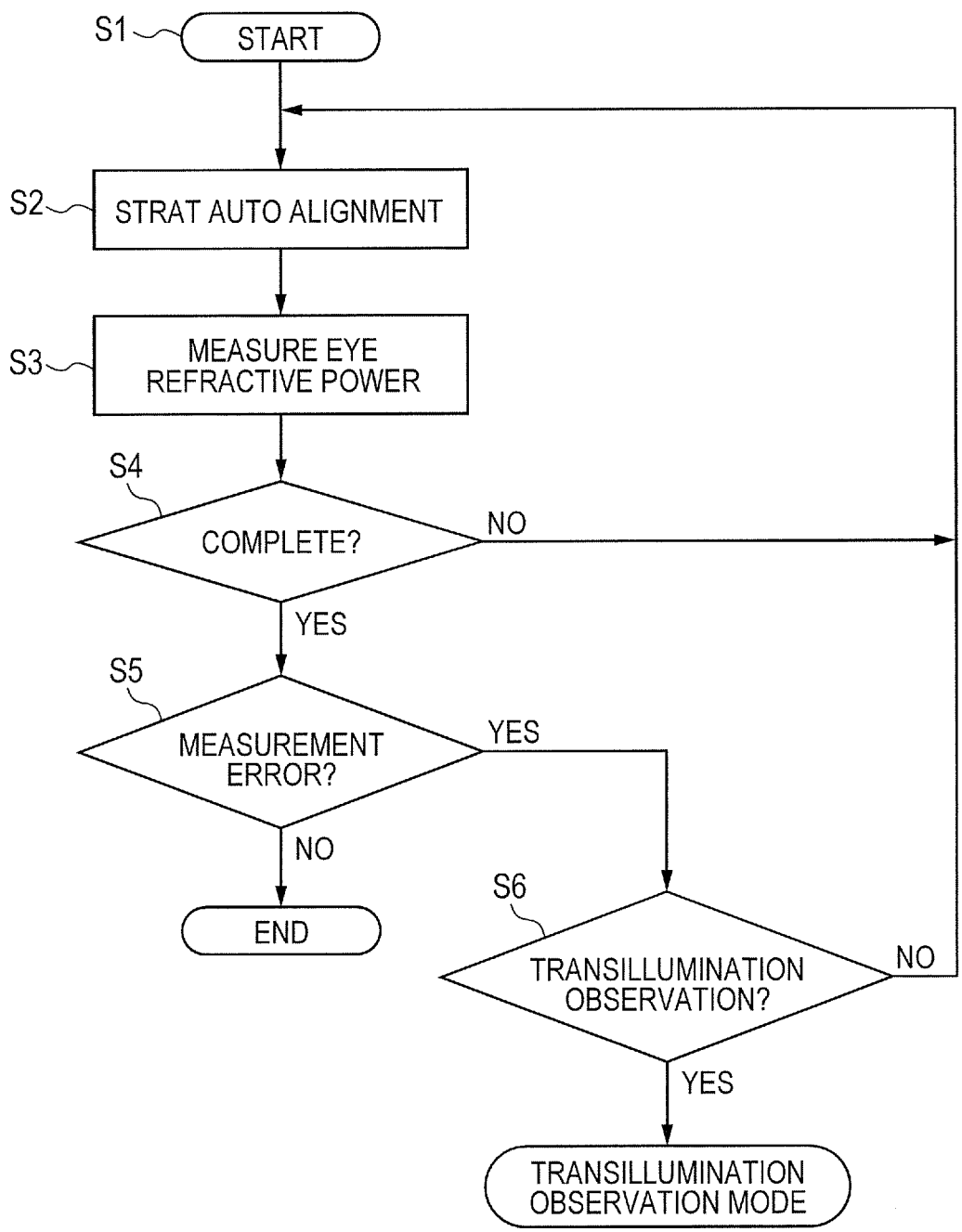
FIG. 12 is a flowchart of an eye refractive power meter according to a third embodiment of the present invention.

FIG. 12 is a flowchart of eye measurement according to the third embodiment of the present invention. A measurement flow is described. In Step S1, the inspector allows the subject to put his or her chin on the chin rest 112 and adjusts a position of the eye to be inspected in the Y axis direction at a predetermined height by the drive mechanism 113. The inspector operates the joystick 101 up to a position where the corneal reflex image of the eye to be inspected E is displayed on the LCD monitor 116, and presses the measurement start switch.

When the measurement start switch is pressed, the automatic alignment of Step S2 is started. The corneal reflex image is extracted from the anterior ocular segment image of the eye to be inspected E stored in the memory 508, and the alignment is performed by the above-mentioned alignment method.

When the alignment is finished, the measurement of Step S3 is performed. The measurement is performed by the above-mentioned eye refractive power measurement method, and the ring image and the measured value are stored in the memory 508. In addition, the anterior ocular segment image of the eye to be inspected E before picking up the ring image is picked up and is stored in the memory 508. In Step S4, it is determined whether or not a plurality of times of successive measurement have been completed. For instance, it is supposed that a completion condition is to perform three times of the successive measurement. When three times of the measurement are not completed, the process returns to Step S2, and the measurement is performed again. When three times of the measurement are completed, the process proceeds to Step S5.

In Step S5, it is determined whether or not a measurement error has occurred. When it is determined that the measurement error has occurred, the process proceeds to Step S6. Note that, in this embodiment, the above-mentioned ring image is an image related to the fundus acquired by illumination of the eye to be inspected, and the image is acquired by the measurement unit 110. In a case that the ring image is partially lost, it is determined that a measurement error has occurred, and the display control unit performs display of the transillumination moving image on the LCD monitor 116. When no measurement error occurs, a measurement result is displayed on the LCD monitor 116, and the measurement is ended. Note that although a case that the ring image is partially lost, an aspect of the present invention is not limited such case. Specifically, in a case that information of an image in connection with the fundus of the eye to be inspected is partially lost, it is preferably determined that the measurement error has occurred.

Figure 13:
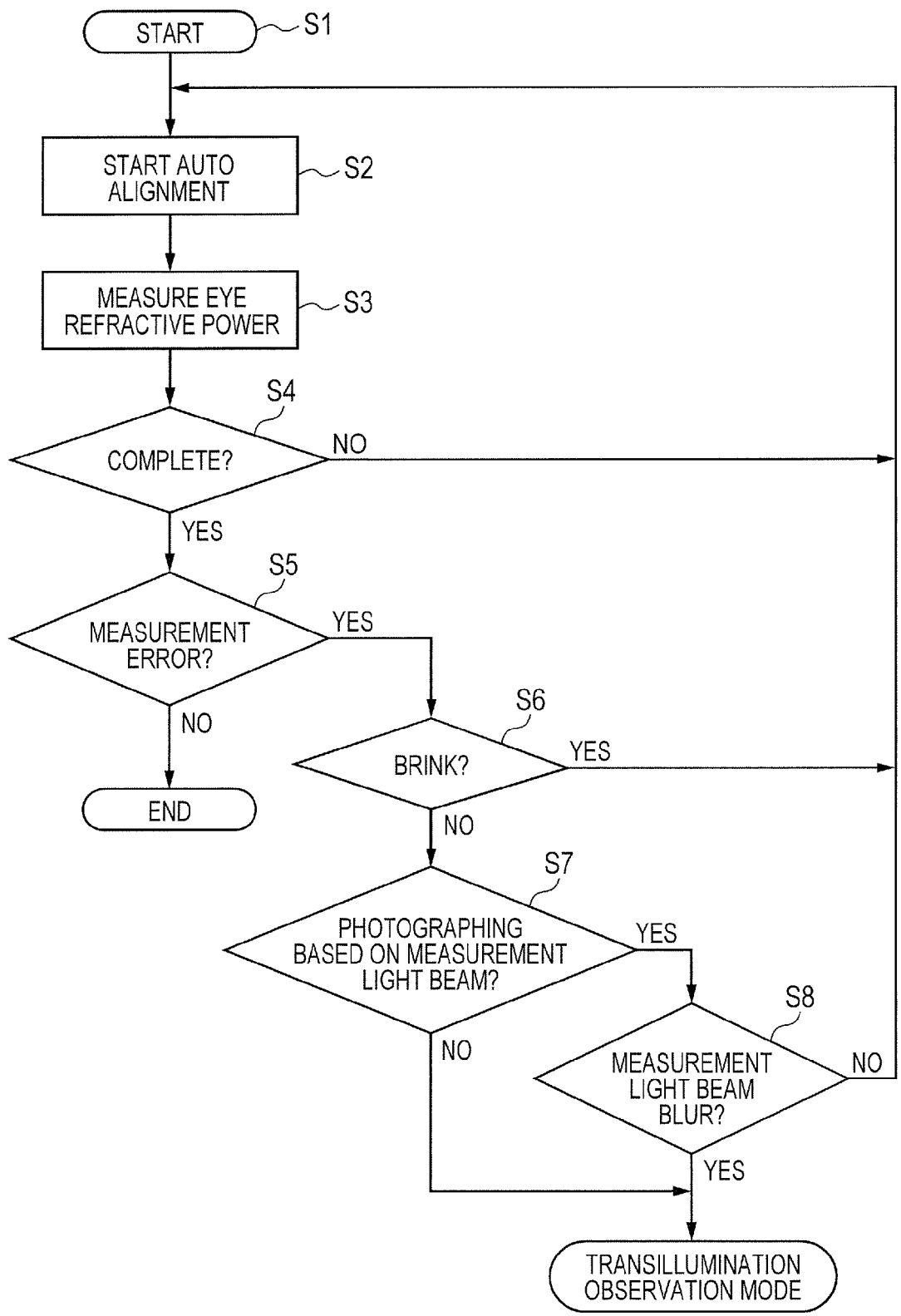
FIG. 13 is a flowchart in consideration of a type of a measurement error.

In Step S6, a type of the measurement error is determined. FIG. 12 illustrates general necessity of the transillumination observation. In a more detailed manner, it is determined as illustrated in FIG. 13 whether or not blinking is detected, whether or not the ring image itself is not picked up, and whether or not the ring image is partially lost or blurred, which can be a cause of the measurement error. Note that, such identification of a cause of error is performed by a module region in the system control portion 501, which functions as a determination unit for determining whether or not the ring image is partially lost. In Step S6, when a measurement error is determined and it is determined that there is a risk of crystalline lens opacity, the eye refractive power measurement mode is automatically changed to the transillumination observation mode. Otherwise, when the ring image cannot be acquired, the system control portion 501 may acquire the ring image again. In this case, the system control portion 501 controls the transillumination image acquiring unit or the transillumination moving image acquiring unit to temporarily stop acquiring the transillumination image as a moving image.

It is further preferred to determine a type of the measurement error by performing a statistical process on the data of a plurality of times of measurement and to determine reliability based on a result of analyzing the ring image. In addition, it is possible to set the number of times of the error determination as a condition for changing to the transillumination observation.

In addition, when occurrence of a measurement error and/or a type of the measurement error that has occurred is displayed on the LCD monitor 116, operability is improved, which is preferred for the inspector.

Second Modified Example

Note that, as a specific information acquiring unit for acquiring the specific information of the eye to be inspected, the eye refractive power measuring unit is described in the above-mentioned embodiments, but the present invention is not limited to this. In other words, the present invention can be similarly applied to a fundus observing and image pickup unit of a fundus camera, a blood flow measuring unit of a fundus blood flow meter, and an image pickup unit of a fundus tomographic imaging apparatus (OCT) using optical interference of a near infrared laser. In addition, the image pickup element may be any one of an area sensor and a line sensor. In addition, it is possible to adopt an eye refractive power measurement apparatus using a measurement principle other than those of the above-mentioned embodiments.

Third Modified Example

In the embodiments described above, there is described the structure in which the light beam is projected from the center of the pupil of the eye to be inspected to the fundus of the eye to be inspected, and the reflection light beam from the fundus of the eye to be inspected is received through the aperture having the ring-like slit from the periphery of the pupil of the eye to be inspected, but the reverse structure may be adopted. In other words, it is possible to adopt a structure in which the light beam is projected from the periphery of the pupil of the eye to be inspected to the fundus of the eye to be inspected through the aperture having the ring-like slit, and the reflection light beam from the fundus of the eye to be inspected is received through the center of the pupil of the eye to be inspected.

Fourth Modified Example

In addition, the present invention further provides an ophthalmologic control method including a step of acquiring specific information of the eye to be inspected, a step of acquiring a transillumination image of the eye to be inspected, and a control step of controlling the transillumination image acquiring unit to acquire the transillumination image as a moving image when the specific information does not satisfy a predetermined condition.

Fourth Embodiment

Next, a fourth embodiment of the present invention is described.

(Flowchart for Alignment and Display Image of Anterior Ocular Segment of Eye to be Inspected)

Figure 14A:
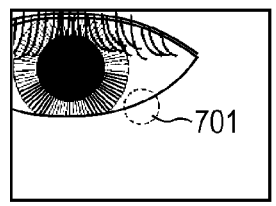
FIGS. 14A, 14B, 14C, 14D, 14E, 14F, 14G, 14H and 14I are diagrams of display images of an anterior ocular segment of the eye to be inspected corresponding to an aligning flow of an ophthalmologic apparatus according to the first embodiment of the present invention.

In the following, alignment control in this apparatus is described with reference to a flowchart of FIG. 15 and display images of the anterior ocular segment illustrated in FIGS. 14A to 14I. The inspector operates the joystick 101 until a part of the pupil of the eye to be inspected is displayed on the LCD monitor 116 and causes the measurement unit 110 to work. FIG. 14A illustrates the anterior ocular segment image in a state where the inspector operates the joystick 101 so that a part of the pupil of the eye to be inspected is displayed. After a part of the pupil is displayed on the LCD monitor 116, the measurement start switch 504 is pressed so that the system control portion 501 starts the automatic alignment control.

Figure 14F:
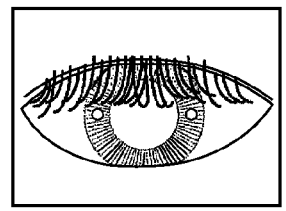
Figure 14B:
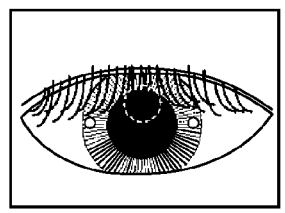
Figure 15:
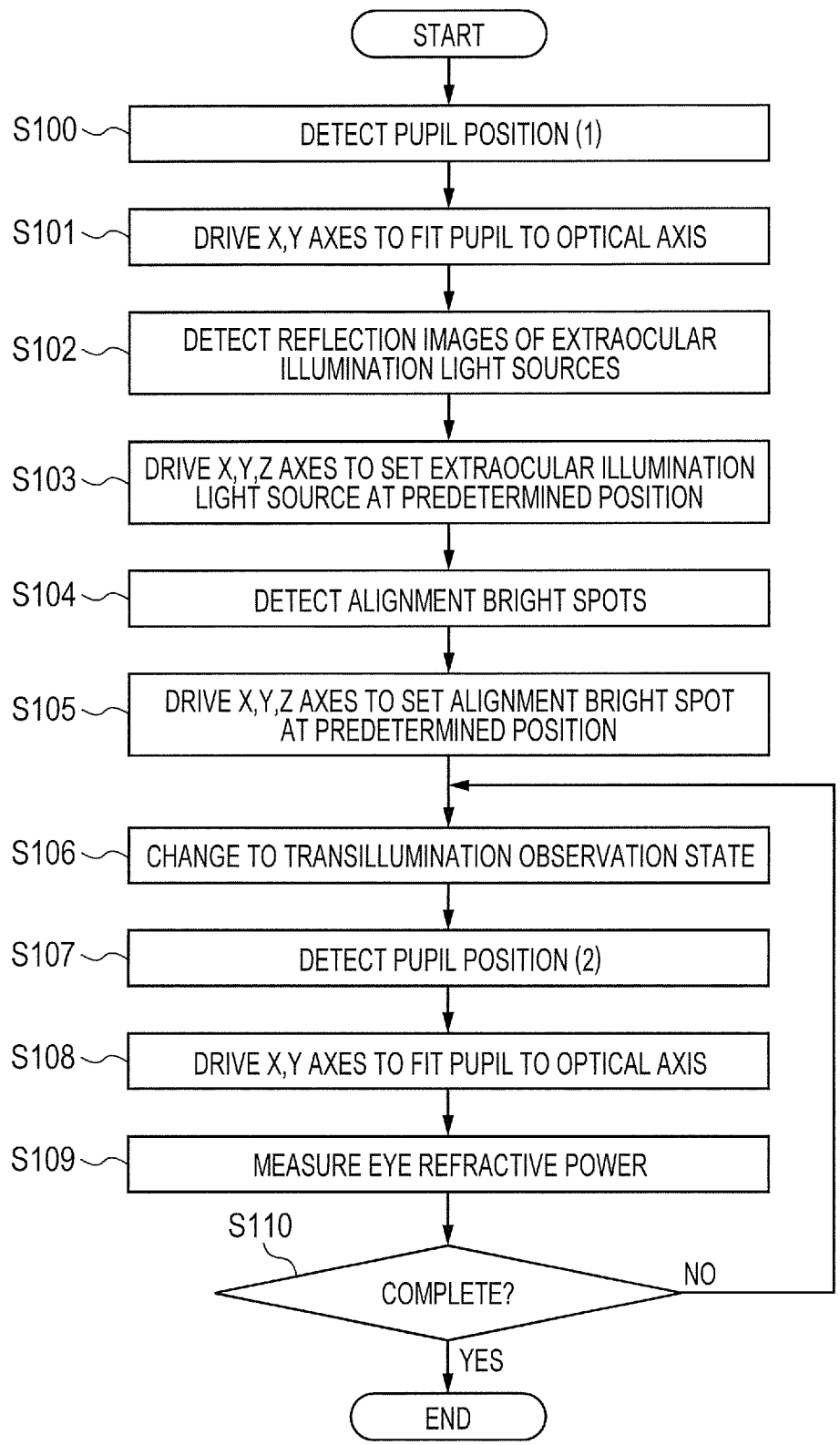
FIG. 15 is a flowchart relating to alignment of an ophthalmologic apparatus according to a fourth embodiment of the present invention.

In Step S100 of FIG. 15, the system control portion 501 analyzes the anterior ocular segment image acquired by the image pickup element 220, and detects the position of the pupil of the eye to be inspected by utilizing the fact that the pupil portion is darker than other portions. When the pupil position is detected, in Step S101, the system control portion 501 performs the X and Y axis motor control by the motor driving unit 514 in such a direction that the pupil center axis matches with the optical axis 01 of the measurement unit 110. FIG. 14B illustrates an anterior ocular segment image in a state where the pupil center axis of the eye to be inspected E substantially matches with the optical axis 01 of the measurement unit 110.

In the following, alignment control using the cornea bright points and alignment control using the transillumination image are described.

(1) Alignment Control Using Cornea Bright Points

Figure 14G:
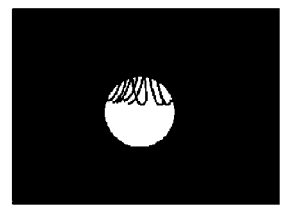
Figure 14C:
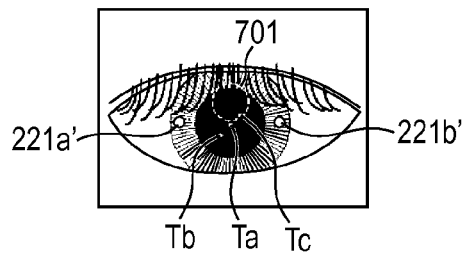

In the state of FIG. 14B, the bright points 221a' and 221b' as reflection light of the anterior ocular segment illumination light sources 221 appear on the anterior ocular segment. In Step S102, the system control portion 501 analyzes the anterior ocular segment image acquired by the image pickup element 220. When the bright points 221a' and 221b' as reflection light of the anterior ocular segment illumination light sources 221 are detected, in Step S103, the system control portion 501 performs the X, Y, and Z axis motor control to set the bright points 221a' and 221b' at predetermined positions and sizes. FIG. 14C illustrates the anterior ocular segment image in which the bright points 221a' and 221b' are set at predetermined positions and sizes.

In the state of FIG. 14C, the above-mentioned bright points Ta, Tb, and Tc for the alignment detection appear. In Step S104, the system control portion 501 analyzes the anterior ocular segment image acquired by the image pickup element 220. When the three bright points Ta, Tb, and Tc are detected, in Step S105, the system control portion 501 controls the motor driving unit 514 and drives the measuring portion 110 in the up-down direction and in the left-right direction so that the center bright point Ta match with the optical axis 01 of the measurement unit 110.

Figure 14H:
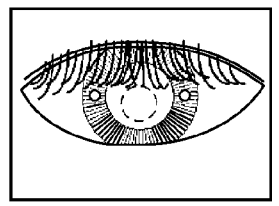
Figure 14D:
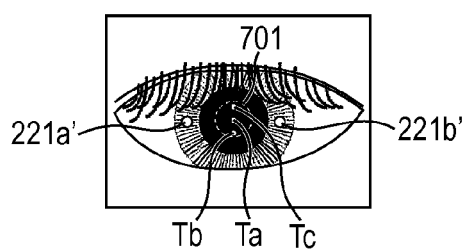

Next, the system control portion 501 further drives the measuring portion 110 in the front-back direction so that the bright points Tb and Tc are arranged in the vertical direction with respect to the bright point Ta, and performs the X, Y, and Z axis control so that the three cornea bright points Ta, Tb, and Tc are aligned in the up-down direction. FIG. 14D illustrates the anterior ocular segment image in a state where the three cornea bright points Ta, Tb, and Tc are aligned in the up-down direction.

Note that, it is known that most human eyes to be inspected have the corneal apex decentered from the pupil center, although depending on individual differences or pathologic factors. Depending on the decentering amount, the reflection light of the fundus may be blocked by the pupil so that a measurement error occurs. Therefore, it is desired to adjust the optical axis of the measuring portion to match with the pupil center. FIG. 14E illustrates the anterior ocular segment image in a state where the cornea bright points Ta, Tb, and Tc are shifted from the pupil center.

(2) Alignment Control Using Transillumination Image

In Step S106, the system control portion 501 changes to the above-mentioned transillumination observation. FIG. 14F illustrates the anterior ocular segment image after changing to the transillumination observation. In Step S107 of FIG. 15, the system control portion 501 analyzes the anterior ocular segment image acquired by the image pickup element 220 and detects the position of the pupil of the eye to be inspected by utilizing the fact that the pupil portion is brighter than other portions. In other words, an area in which luminance of the bright portion in the acquired anterior ocular segment image is a predetermined value or higher is extracted as the pupil area of the eye to be inspected. This extracting operation is performed by a module region which functions as a pupil extracting unit in the system control portion 501. FIG. 14G illustrates the anterior ocular segment image in a state where the pupil is binarized and is extracted as a bright portion.

In this embodiment, a barycenter position of the binarized bright portion is detected as a pupil center. When the pupil position is detected, in Step S108, the system control portion 501 performs the X and Y axis motor control by the motor driving unit 514 in such a direction that the pupil center axis matches with the optical axis 01 of the measurement unit 110. More specifically, after the system control portion 501 controls the driving unit so as to perform the alignment based on the pupil area, the driving unit is controlled so that the alignment is performed by using the changed reference position.

In other words, the above-mentioned changing unit changes the reference position based on the extracted pupil area. FIG. 14H illustrates a state where the pupil center axis of the eye to be inspected E matches with the optical axis 01 of the measurement unit 110. Thus, the alignment is completed.

Figure 14I:
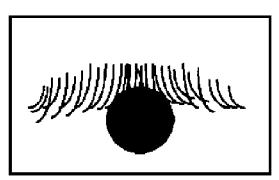
Figure 14E:
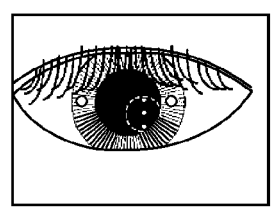

Note that, FIG. 14I illustrates an anterior ocular segment image after a binarizing process utilizing the fact that the pupil portion is darker than other portions when analyzing the anterior ocular segment image acquired by the image pickup element 220 in the pupil position detection (1) in Step S100. Compared with the anterior ocular segment image of FIG. 14H binarized regarding the pupil as a bright portion in Step S107, lashes are also detected as a dark portion in addition to the pupil in FIG. 14I so that a detection error occurs. In contrast, in FIG. 14H, lashes are detected as a dark portion while the pupil area can be detected as a bright portion, and hence it is possible to prevent occurrence of a detection error.

When the alignment is completed, in Step S109, the system control portion 501 measures the eye refractive power. In Step S110, the system control portion 501 determines the measurement completion condition such as a predetermined number of times of measurement, and returns to Step S106 and repeats the process of Step S106 to Step S110 until the completion condition is satisfied. When the completion condition is satisfied, the measurement result (result of acquiring the specific information) is displayed on the LCD monitor 116, and the measurement is finished.

Fifth Embodiment

This embodiment is described with reference to a flowchart of FIG. 16 and picked-up anterior ocular segment images of FIGS. 17A and 17B. Unlike the first embodiment, the alignment control is performed not only in the left-right direction (X direction) and the up-down direction (Y direction) but also in the front-back direction (Z direction) in the alignment control using the transillumination image in this embodiment. The process from the alignment start to Step S105 is the same as that in the first embodiment, and hence description thereof is omitted.

Figure 17A:
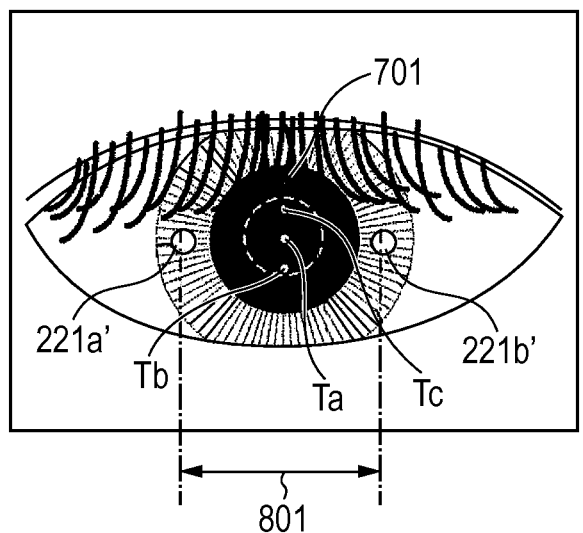
FIG. 17A is a diagram illustrating an anterior ocular segment image in a state where automatic alignment is completed.

In Step S105, the system control portion 501 performs the X, Y, and Z axis control, and hence the three cornea bright points Ta, Tb, and Tc are aligned in the up-down direction in the anterior ocular segment image as illustrated in FIG. 17A. Next, in Step S200, the system control portion 501 stores an interval 801 between the bright points 221a' and 221b' as the reflection light of the anterior ocular segment illumination light sources 221, when the cornea bright points Ta, Tb, and Tc in the state of FIG. 17A are aligned in the up-down direction so that the automatic alignment is completed. Then, the system control portion 501 changes to the above-mentioned transillumination observation in Step S201.

In Step S202, the system control portion 501 extracts the position of the pupil of the eye to be inspected as a bright portion similarly to Step S107 of FIG. 15 of the fourth embodiment, and detects an interval 801' between the bright points 221a' and 221b' as the reflection light of the anterior ocular segment illumination light sources 221 at that time. FIG. 17B illustrates the anterior ocular segment image in the state changed to the transillumination observation. When the pupil position is extracted, in Step S203, the system control portion 501 performs the X and Y axis motor control by the motor driving unit 514 in such a direction that the pupil center axis matches with the optical axis 01 of the measurement unit 110.

Next, in Step S204, the system control portion 501 performs control so that the interval 801' between the bright points 221a' and 221b' as the reflection light of the anterior ocular segment illumination light sources 221 becomes equal to the interval 801 between the bright points stored in Step S200. In other words, the system control portion 501 performs the Z axis motor control by the motor driving unit 514, and hence the alignment is completed. Then, the system control portion 501 performs the measurement of the eye refractive power and ends the measurement in accordance with a predetermined condition similarly to the fourth embodiment.

Sixth Embodiment

Figure 16:
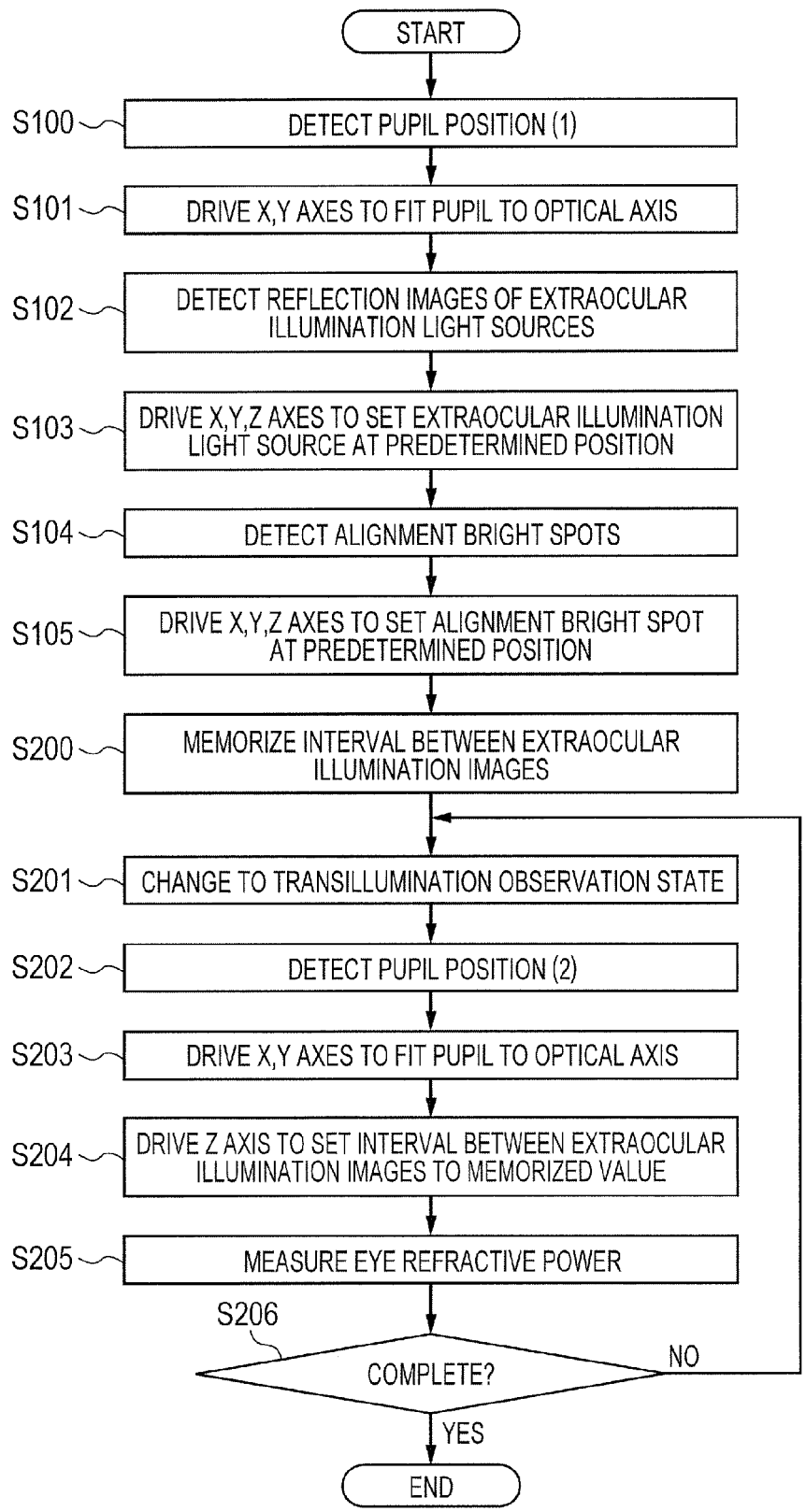
FIG. 16 is a flowchart relating to alignment of an ophthalmologic apparatus according to a fifth embodiment of the present invention.
Figure 17B:
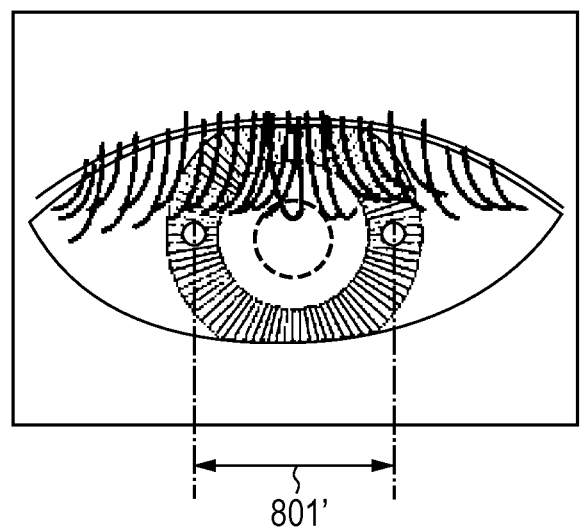
FIG. 17B is a diagram illustrating an anterior ocular segment image after changing to transillumination observation.
Figure 18A:
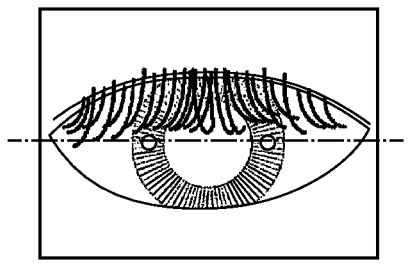
Figure 18B:
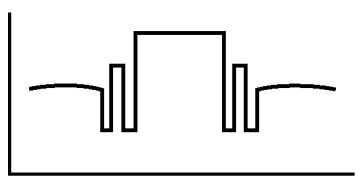

In Step S107 of FIG. 15 of the fourth embodiment, and in Step S202 of FIG. 16 of the fifth embodiment, the position of the pupil of the eye to be inspected is extracted by utilizing the fact that the pupil portion is brighter than other portions, but more accurate pupil extraction is performed in this step of this embodiment. FIG. 18A illustrates the anterior ocular segment image in a state of the transillumination observation, and FIG. 18B illustrates a luminance distribution on one central horizontal line in FIG. 18A. For instance, when external light is strong, even if the anterior ocular segment illumination light is adjusted, the surrounding is brighter than the pupil portion so that it may be impossible to detect only the pupil portion.

Figure 18C:
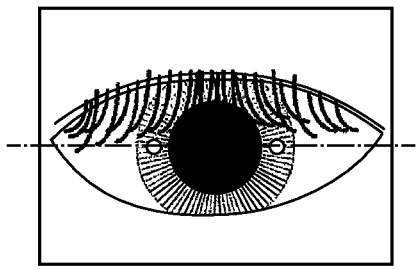
Figure 18D:
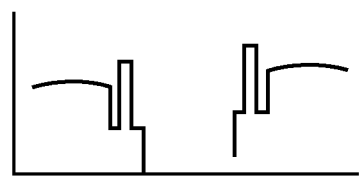

In this embodiment, immediately after storing the transillumination observation image as the anterior ocular segment image when the fundus illumination light source is turned on as illustrated in FIG. 18A, the fundus illumination light source is turned off, and the ordinary anterior ocular segment image is also stored. FIG. 18C illustrates an anterior ocular segment image when the fundus illumination light source is turned off, and FIG. 18D illustrates a luminance distribution on one central horizontal line in FIG. 18C. In detection of the pupil portion, the system control portion 501 subtracts the anterior ocular segment image of FIG. 18C from the stored anterior ocular segment image of FIG. 18A, and hence it is possible to securely detect the pupil portion without being affected by external light or the like. In other words, in this embodiment, using the fundus illumination light source for generating light for illuminating the fundus of the eye to be inspected for acquiring the transillumination moving image, the above-mentioned pupil extracting unit extracts the image, in which the anterior ocular segment image in the state of turning off the fundus illumination light source is extracted, as the pupil area of the anterior ocular segment, from the transillumination moving image of the anterior ocular segment of the eye to be inspected in the state of turning on the fundus illumination light source.

Figure 18E:
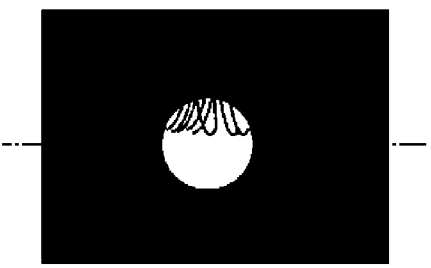
Figure 18F:
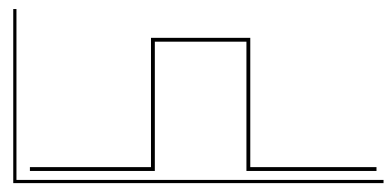

FIG. 18E illustrates an image obtained by subtracting the anterior ocular segment image of FIG. 18C from the stored anterior ocular segment image of FIG. 18A, and FIG. 18F illustrates a luminance distribution on one central horizontal line in FIG. 18E. Note that, description of parts other than the pupil detection step is the same as that in the fourth embodiment.

Fifth Modified Example

In the embodiments described above, when the pupil portion is detected, a barycenter portion thereof is detected by the binarizing process, but the present invention is not limited to this. For instance, it is possible to detect the contour of the pupil and to determine the center by approximating the contour by a circle or the like.

Sixth Modified Example

In addition, in the embodiments described above, the eye refractive power meter is described. However, the present invention can be similarly applied to other ophthalmologic apparatus such as a fundus camera, a fundus blood flow meter, a fundus tomographic imaging apparatus (OCT) utilizing optical interference of a near infrared laser.

Other Modified Examples

Further, the present invention may also be realized by executing the following process. Specifically, software (program) for realizing the functions of the embodiments described above is supplied to a system or an apparatus via a network or an arbitrary type of storage medium, and a computer (CPU or MPU) of the system or the apparatus reads and executes the program.

According to the present invention, it is possible to provide the ophthalmologic apparatus which automatically changes to the transillumination observation mode (in which the transillumination image is acquired as a moving image) when a measurement error occurs.

In addition, according to the present invention, it is possible to provide the ophthalmologic apparatus that can accurately detect a pupil position so as to perform accurate alignment. In other words, because the pupil position can be accurately detected by using the transillumination image, accurate alignment can be performed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-279990, filed Dec. 21, 2011, Japanese Patent Application No. 2011-279582, filed Dec. 21, 2011, Japanese Patent Application No. 2011-279586, filed Dec. 21, 2011, and Japanese Patent Application No. 2012-267288, filed Dec. 6, 2012 which are hereby incorporated by reference herein in their entirety.

What is claimed is:

1. An ophthalmologic apparatus comprising:
   a measuring unit which measures information of an eye to be inspected by illuminating the eye to be inspected;
   a driving unit which drives the measuring unit;
   a transillumination moving image acquiring unit which acquires a transillumination moving image of the eye to be inspected;
   a display control unit which controls a display unit to display the transillumination moving image;
   a changing unit which changes a reference position for performing alignment between the eye to be inspected and the measuring unit in the transillumination moving image displayed on the display unit; and
   a control unit which controls the driving unit so as to perform the alignment by using the changed reference position.

2. An ophthalmologic apparatus according to claim 1, wherein the control unit controls the driving unit so as to perform the alignment by using the changed reference position every time the measuring unit measures the information of the eye to be inspected a plurality of times.

3. An ophthalmologic apparatus according to claim 1, further comprising a pupil extracting unit which extracts, as a pupil area of the eye to be inspected, an area in the transillumination moving image in which luminance is a predetermined value or higher.

4. An ophthalmologic apparatus according to claim 3, wherein the control unit controls the driving unit so as to perform the alignment by using the changed reference position after controlling the driving unit so as to perform the alignment based on the pupil area.

5. An ophthalmologic apparatus according to claim 3, wherein the changing unit changes the reference position based on the pupil area.

6. An ophthalmologic apparatus according to claim 1, further comprising:
   a fundus illumination light source which generates light for illuminating a fundus of the eye to be inspected for acquiring the transillumination moving image; and
   a pupil extracting unit which extracts, as a pupil area of an anterior ocular segment, an image obtained by extracting an image of the anterior ocular segment in a state of turning off the fundus illumination light source from the transillumination moving image of the anterior ocular segment of the eye to be inspected in a state of turning on the fundus illumination light source.

7. An ophthalmologic apparatus according to claim 1, wherein the control unit controls the driving unit so as to perform the alignment between the eye to be inspected and an optical axis of the measuring unit by using the changed reference position.

8. An ophthalmologic apparatus according to claim 1, further comprising an operation unit for manually operating the driving unit,
   wherein the control unit controls the driving unit to offset a position of an optical axis of the measuring unit.

9. An ophthalmologic apparatus according to claim 1, wherein the measuring unit acquires an image of a fundus of the eye to be inspected by illuminating the eye to be inspected, and wherein the display control unit controls the display unit to display the transillumination moving image acquired by the transillumination moving image acquiring unit in a case where information of the fundus, in the acquired image of the fundus, is partially lost.

10. An ophthalmologic apparatus according to claim 9, wherein the control unit controls the measuring unit to acquire the image of the fundus again in a case where the measuring unit fails to acquire the image of the fundus.

11. An ophthalmologic apparatus according to claim 9, further comprising a determination unit which determines whether or not the information of the fundus in the acquired image of the fundus is partially lost in a case where the information of the eye to be inspected that is measured by the measuring unit has an error.

12. An ophthalmologic apparatus according to claim 9, wherein in a case where the measuring unit fails to acquire the image on the fundus, the control unit controls the transillumination moving image acquiring unit to avoid acquiring the transillumination moving image as a moving image and controls the measuring unit to acquire the image on the fundus again.

13. An ophthalmologic apparatus according to claim 9, wherein the measuring unit measures information on the eye to be inspected by illuminating the eye to be inspected with light based on the image of the fundus.

14. An ophthalmologic apparatus according to claim 9, wherein the control unit controls the display unit to display a display form indicating a state of the image of the fundus in a case where the information of the fundus in the acquired image of the fundus is partially lost.

15. An ophthalmologic method comprising:

displaying a transillumination moving image of an eye to be inspected on a display unit;

changing a reference position for performing alignment between the eye to be inspected and a measuring unit, which measures information of the eye to be inspected by illuminating the eye to be inspected, in the transillumination moving image displayed on the display unit; and performing the alignment by using the changed reference position.

16. A recording medium having a program recorded thereon, the program causing a computer to perform the steps of the ophthalmologic method according to claim 15.

17. An ophthalmologic method according to claim 15, further comprising:

acquiring an image of a fundus of the eye to be inspected;

acquiring an image of an anterior ocular segment of the eye to be inspected; and acquiring the image of the anterior ocular segment as a transillumination moving image in a case where information of the fundus in the acquired image of the fundus is partially lost.

18. A recording medium having a program recorded thereon, the program causing a computer to perform the steps of the ophthalmologic method according to claim 17.

* * * * *